US006566385B2

(12) United States Patent
deSolms et al.

(10) Patent No.: US 6,566,385 B2
(45) Date of Patent: May 20, 2003

(54) INHIBITORS OF PRENYL-PROTEIN TRANSFERASE

(75) Inventors: S. Jane deSolms, Collegeville, PA (US); Gerald E. Stokker, Gwynedd Valley, PA (US); Anthony W. Shaw, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 9 days.

(21) Appl. No.: 09/757,217

(22) Filed: Jan. 9, 2001

(65) Prior Publication Data

US 2002/0099007 A1 Jul. 25, 2002

Related U.S. Application Data

(60) Provisional application No. 60/175,801, filed on Jan. 12, 2000.

(51) Int. Cl.⁷ ................. A61K 31/4178; C07D 498/22; C07D 493/18; A61P 35/00
(52) U.S. Cl. ................ 514/397; 540/456; 540/468; 548/311.7
(58) Field of Search ................ 540/456, 468; 548/311.7; 514/397

(56) References Cited

U.S. PATENT DOCUMENTS

| | | | |
|---|---|---|---|
| 5,672,611 A | 9/1997 | Doll et al. | 514/325 |
| 5,714,609 A | 2/1998 | Doll et al. | 546/93 |
| 5,721,236 A | 2/1998 | Bishop et al. | 514/255 |
| 5,756,528 A | 5/1998 | Anthony et al. | 514/399 |
| 5,780,488 A | 7/1998 | Bergman et al. | 514/357 |
| 5,801,175 A | 9/1998 | Afonso et al. | 514/254 |
| 5,891,872 A | 4/1999 | Doll et al. | 514/220 |
| 5,914,341 A | 6/1999 | Dinsmore et al. | 514/396 |
| 5,922,883 A | 7/1999 | Hutchinson | 548/338.1 |
| 5,968,965 A | 10/1999 | Dinsmore et al. | 514/399 |
| 5,981,562 A | 11/1999 | Dinsmore et al. | 514/400 |
| 6,028,201 A | 2/2000 | Dinsmore et al. | 548/338.1 |

FOREIGN PATENT DOCUMENTS

| | | |
|---|---|---|
| WO | WO 98/11091 | 3/1998 |
| WO | WO 00/01382 | 1/2000 |
| WO | WO 00/01701 | 1/2000 |
| WO | WO 00/01702 | 1/2000 |

OTHER PUBLICATIONS

T. M. Williams, Inhibitors of protein farnesylation 1998, Exp. Opin. Ther. Patents, vol. 8(5), pp. 553–569.
T. M. Williams, Inhibitors of protein prenylation 1999, Exp. Opin. Ther. Patents, vol. 9(9) pp. 1263–1280.
I. M. Bell, Inhibitors of protein prenylation 2000, Exp. Opin. Ther. Patents, vol. 10(12) 1813–1831.

N. E. Kohl et al., Inhibition of farnesultransferase induces regression of mammary and salivary carcinomas in rats transgenic mice, Nature Medicine, vol. 1, No. 8, pp. 792–797, Aug. 1995.

N. E. Kohl et al., Protein farnesyltransferase inhibitors block the growth of ras–dependent tumors in nude mice, Proc. Natl. Acad. Sci. USA, vol. 91, pp. 9141–9145, Sep. 1994.

T. M. Williams et al., N–Arylpiprazinone Inhibitors of Farnesyltransferase: Discovery and Biological Activity, J. Med. Chem., vol. 42, pp. 3779–3784, 1999.

B. N. Balasubramanian et al., Recent Developments in Cancer Cytotoxics, Annual Reports in Medicinal Chemistry, vol. 33, Chapter 17, pp. 151–162, 1998.

G. L. Bolton et al., Ras Oncogene Directed Approaches in Cancer Chemotherapy, Annual Reports in Medicinal Chemistry, vol. 29, Chapter 17, pp. 165–174, 1998.

S.L. Graham, Inhibitors of protein farnesylation: a new approach to cancer chemotherapy, Exp. Opin. Ther. Patents, vol. 5(12), pp. 1269–1285, 1995.

S. L. Graham et al., Inhibitors of protein farnesylation, Exp. Opin. Ther. Patents, vol. 6(12), pp. 1295–1304, 1996.

L. Sepp–Lorenzino et al., A Peptidomimetic Inhibitor of Farnesyl:Protein Transferase Blocks the Anchorage–dependent and –independent Growth of Human Tumor Cell Lines, Cancer Research, vol. 55, pp. 5302–5309, 1995.

A. A. Adjei et al., A Phase I Trial of the Farnesyl Transferase Inhibitor SCH66336: Evidence for Biological and Clinical Activity, Cancer Research, pp. 1871–1877, Apr. 2000.

J. Zujewski et al., Phase I and Pharmacokinetic Study of Farnesyl Protein Transferase Inhibitor R115777 in Advanced Cancer, Journal of Clinical Oncology, vol. 18, No. 4, pp. 927–941, Feb. 2000.

*Primary Examiner*—Bruck Kifle
(74) *Attorney, Agent, or Firm*—Dianne Brown; Mark R. Daniel; Matthew A. Leff

(57) ABSTRACT

The present invention is directed to peptidomimetic macrocyclic compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

22 Claims, No Drawings

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: N-terminus of Ras protein

<400> SEQUENCE: 1

Cys Val Leu Leu
 1

<210> SEQ ID NO 2
<211> LENGTH: 4
<212> TYPE: PRT
<213> ORGANISM: Artificial Sequence
<220> FEATURE:
<223> OTHER INFORMATION: N-terminus of Ras protein

<400> SEQUENCE: 2

Cys Val Leu Ser
 1

<210> SEQ ID NO 3
<211> LENGTH: 15
<212> TYPE: PRT
<213> ORGANISM: Artificial Sequence
<220> FEATURE:
<223> OTHER INFORMATION: Completely Synthetic Amino Acid

<400> SEQUENCE: 3

Gly Lys Lys Lys Lys Lys Lys Ser Lys Thr Lys Cys Val Ile Met
 1               5                  10                  15

<210> SEQ ID NO 4
<211> LENGTH: 52
<212> TYPE: DNA
<213> ORGANISM: Artificial Sequence
<220> FEATURE:
<223> OTHER INFORMATION: Artificial Nucleotide Sequence

<400> SEQUENCE: 4
gagagggaat cgggcccttt cctgcatgct gctgctgctg ctgctgctgg gc            52

<210> SEQ ID NO 5
<211> LENGTH: 41
<212> TYPE: DNA
<213> ORGANISM: Artificial Sequence
<220> FEATURE:
<223> OTHER INFORMATION: Artificial Antisense Nucleotide Sequence

<400> SEQUENCE: 5
gagagagctc gaggttaacc cgggtgcgcg gcgtcggtgg t                       41

<210> SEQ ID NO 6
<211> LENGTH: 42

<212> TYPE: DNA
<213> ORGANISM: Artificial Sequence
<220> FEATURE:
<223> OTHER INFORMATION: Artificial Nucleotide Sequence

<400> SEQUENCE: 6
gagagagtct agagttaacc cgtggtcccc gcgttgcttc ct                42

<210> SEQ ID NO 7
<211> LENGTH: 43
<212> TYPE: DNA
<213> ORGANISM: Artificial Sequence
<220> FEATURE:
<223> OTHER INFORMATION: Artificial Antisense Nucleotide Sequence

<400> SEQUENCE: 7
gaagaggaag cttggtaccg ccactgggct gtaggtggtg gct               43

<210> SEQ ID NO 8
<211> LENGTH: 27
<212> TYPE: DNA
<213> ORGANISM: Artificial Sequence
<220> FEATURE:
<223> OTHER INFORMATION: Artificial Nucleotide Sequence

<400> SEQUENCE: 8
ggcagagctc gtttagtgaa ccgtcag                                 27

<210> SEQ ID NO 9
<211> LENGTH: 27
<212> TYPE: DNA
<213> ORGANISM: Artificial Sequence
<220> FEATURE:
<223> OTHER INFORMATION: Artificial Antisense Nucleotide Sequence

<400> SEQUENCE: 9
gagagatctc aaggacggtg actgcag                                 27

<210> SEQ ID NO 10
<211> LENGTH: 86
<212> TYPE: DNA
<213> ORGANISM: Artificial Sequence
<220> FEATURE:
<223> OTHER INFORMATION: Artificial Nucleotide Sequence

<400> SEQUENCE: 10
tctcctcgag gccaccatgg ggagtagcaa gagcaagcct aaggacccca gccagcgccg    60
gatgacagaa tacaagcttg tggtgg                                       86

<210> SEQ ID NO 11
<211> LENGTH: 33
<212> TYPE: DNA
<213> ORGANISM: Artificial Sequence
<220> FEATURE:
<223> OTHER INFORMATION: Artificial Antisense Nucleotide Sequence

<400> SEQUENCE: 11
cacatctaga tcaggacagc acagacttgc agc                          33

<210> SEQ ID NO 12
<211> LENGTH: 41
<212> TYPE: DNA
<213> ORGANISM: Artificial Sequence
<220> FEATURE:
<223> OTHER INFORMATION: Artificial Nucleotide Sequence

<400> SEQUENCE: 12
tctcctcgag gccaccatga cagaatacaa gcttgtggtg g    41

<210> SEQ ID NO 13
<211> LENGTH: 38
<212> TYPE: DNA
<213> ORGANISM: Artificial Sequence
<220> FEATURE:
<223> OTHER INFORMATION: Artificial Antisense Nucleotide Sequence

<400> SEQUENCE: 13
cactctagac tggtgtcaga gcagcacaca cttgcagc    38

<210> SEQ ID NO 14
<211> LENGTH: 38
<212> TYPE: DNA
<213> ORGANISM: Artificial Sequence
<220> FEATURE:
<223> OTHER INFORMATION: Artificial Nucleotide Sequence

<400> SEQUENCE: 14
gagagaattc gccaccatga cggaatataa gctggtgg    38

<210> SEQ ID NO 15
<211> LENGTH: 33
<212> TYPE: DNA
<213> ORGANISM: Artificial Sequence
<220> FEATURE:
<223> OTHER INFORMATION: ArtificialAntisense Nucleotide Sequence

<400> SEQUENCE: 15
gagagtcgac gcgtcaggag agcacacact tgc    33

<210> SEQ ID NO 16
<211> LENGTH: 22
<212> TYPE: DNA
<213> ORGANISM: Artificial Sequence
<220> FEATURE:
<223> OTHER INFORMATION: Artificial Nucleotide Sequence

<400> SEQUENCE: 16
ccgccggcct ggaggagtac ag    22

<210> SEQ ID NO 17
<211> LENGTH: 38
<212> TYPE: DNA
<213> ORGANISM: Artificial Sequence
<220> FEATURE:
<223> OTHER INFORMATION: Artificial Nucleotide Sequence

<400> SEQUENCE: 17
gagagaattc gccaccatga ctgagtacaa actggtgg    38

<210> SEQ ID NO 18
<211> LENGTH: 32
<212> TYPE: DNA
<213> ORGANISM: Artificial Sequence
<220> FEATURE:
<223> OTHER INFORMATION: Artificial Antisense Nucleotide Sequence

<400> SEQUENCE: 18
gagagtcgac ttgttacatc accacacatg gc    32

<210> SEQ ID NO 19
<211> LENGTH: 21

```
<212> TYPE: DNA
<213> ORGANISM: Artificial Sequence
<220> FEATURE:
<223> OTHER INFORMATION: Artificial Nucleotide Sequence

<400> SEQUENCE: 19
gttggagcag ttggtgttgg g                                        21

<210> SEQ ID NO 20
<211> LENGTH: 38
<212> TYPE: DNA
<213> ORGANISM: Artificial Sequence
<220> FEATURE:
<223> OTHER INFORMATION: Artificial Antisense Nucleotide Sequence

<400> SEQUENCE: 20
gagaggtacc gccaccatga ctgaatataa acttgtgg                      38

<210> SEQ ID NO 21
<211> LENGTH: 36
<212> TYPE: DNA
<213> ORGANISM: Artificial Sequence
<220> FEATURE:
<223> OTHER INFORMATION: Artificial Nucleotide Sequence

<400> SEQUENCE: 21
ctctgtcgac gtatttacat aattacacac tttgtc                        36

<210> SEQ ID NO 22
<211> LENGTH: 24
<212> TYPE: DNA
<213> ORGANISM: Artificial Sequence
<220> FEATURE:
<223> OTHER INFORMATION: Artificial Nucleotide Sequence

<400> SEQUENCE: 22
gtagttggag ctgttggcgt aggc                                     24

<210> SEQ ID NO 23
<211> LENGTH: 38
<212> TYPE: DNA
<213> ORGANISM: Artificial Sequence
<220> FEATURE:
<223> OTHER INFORMATION: Artificial Nucleotide Sequence

<400> SEQUENCE: 23
gagaggtacc gccaccatga ctgaatataa acttgtgg                      38

<210> SEQ ID NO 24
<211> LENGTH: 45
<212> TYPE: DNA
<213> ORGANISM: Artificial Sequence
<220> FEATURE:
<223> OTHER INFORMATION: Artificial Antisense Nucleotide Sequence

<400> SEQUENCE: 24
ctctgtcgac agattacatt ataatgcatt ttttaatttt cacac              45

<210> SEQ ID NO 25
<211> LENGTH: 24
<212> TYPE: DNA
<213> ORGANISM: Artificial Sequence
```

```
<220> FEATURE:
<223> OTHER INFORMATION: Artificial Nucleotide Sequence

<400> SEQUENCE: 25
gtagttggag ctgttggcgt aggc                                          24
```

INHIBITORS OF PRENYL-PROTEIN TRANSFERASE

RELATED APPLICATION

The present patent application is a continuation-in-part application of copending provisional application Serial No. 60/175,801, filed Jan. 12, 2000.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The term prenyl-protein transferase may be used to generally refer to farnesyl-protein transferase and geranylgeranyl-protein transferase. The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994) and induces regression of mammary and salivary carcinomas in ras transgenic mice (N. E. Kohl et al., *Nature Medicine,* 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol Chem.,* 265:14701–14704 (1990); Schafer et al., *Science,* 249:1133–1139 (1990); Manne et al., *Proc. Natl. Acad. Sci USA,* 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises peptidomimetic macrocyclic compounds which inhibit the prenyl-protein transferase. Further contained in this invention are chemotherapeutic compositions containing these prenyl-protein transferase inhibitors and methods for their production.

The compounds of this invention are illustrated by the formula A:

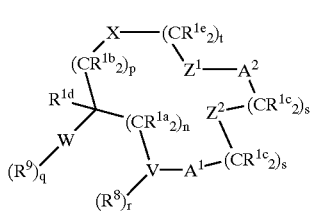

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

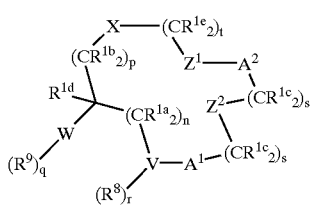

wherein:

$R^{1a}$, $R^{1b}$, $R^{1c}$, $R^{1d}$ and $R^{1e}$ are independently selected from:

a) hydrogen, b) unsubstituted or substituted aryl, unsubstituted or substituted heterocycle, $C_3$–$C_{10}$ cycloalkyl, $C_1$–$C_6$ perfluoroalkyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $(R^{10})_2N$—$C(O)NR^{10}$—, $R^{10}C(O)$—, $R^{10}OC(O)$—, —$N(R^{10})_2$, or $R^{11}OC(O)NR^{10}$—, c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, $C_1$–$C_6$ perfluoroalkyl, halogen, $R^{10}O$—, $R^4S(O)_m$—, $R^4S(O)_2NR^{10}$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, —$N(R^{10})_2$, and $R^{11}OC(O)$—$NR^{10}$—;

or two $R^{1a}$s, two $R^{1b}$s, two $R^{1c}$s or two $R^{1e}$s, on the same carbon atom may be combined to form —$(CH_2)_y$—, wherein one of the $CH_2$ moieties is optionally replaced with —C(=O)—, —NH— or —NHC(=O)—;

$R^4$ is selected from $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO, e)

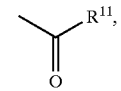

f) —$SO_2R^{11}$ g) $N(R^{10})_2$, or h) $C_{1-4}$perfluoroalkyl;

$R^6$ and $R^7$ are independently selected from:

1) hydrogen,

2) $R^{10}C(O)$—, or $R^{10}OC(O)$—, and

3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, unsubstituted or substituted with one or more substituents selected from:

a) $R^{10}O$—, b) aryl or heterocycle, c) halogen, d) $R^{10}C(O)NR^{10}$—, e)

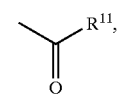

f) —$SO_2R^{11}$ g) $N(R^{10})_2$, h) $C_{3-6}$ cycloalkyl, i) $C_1$–$C_6$ perfluoroalkyl, j) $(R^{10})_2N$—$C(NR^{10})$—, k) $R^{10}OC(O)$—, l) $R^{11}OC(O)NR^{10}$—, m) CN, and n) $NO_2$, or $R^6$ and $R^7$ may be joined in a ring;

$R^8$ is independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, —$N(R^{10})_2$, or $R^{11}OC(O)NR^{10}$—, and c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{11}C(O)$—, $R^{10}OC(O)$—, —$N(R^{10})_2$, or $R^{10}OC(O)NH$—;

$R^9$ is selected from:

a) hydrogen, b) $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, —$N(R^{10})_2$, or $R^{11}OC(O)NR^{10}$—, and c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, unsubstituted or substituted benzyl, unsubstituted or substituted aryl and unsubstituted or substituted heterocycle;

$R^{11}$ is independently selected from $C_1$–$C_6$ alkyl unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, and S(O)$_m$;

$A^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{11}$)S(O)$_2$—, —NR$^{10}$C(O)NR$^{10}$—, S(O)$_m$ and —C(R$^{1c}$)$_2$—;

W is heteroaryl;

V is selected from:
  a) heteroaryl, and
  b) aryl;

X is selected from —C(O)—, —C(O)NR$^{10}$—, —NR$^{10}$C(O)—, —NR$^{10}$C(O)—O—, —O—C(O)NR$^{10}$—, —NR$^{10}$C(O)NR$^{10}$—, O, —N(R$^{10}$)—, —S(O)$_2$N(R$^{10}$)—, —N(R$^{11}$)S(O)$_2$— and S(O)$_m$;

$Z^1$ is selected from unsubstituted or substituted aryl and unsubstituted or substituted heterocycle, wherein the substituted aryl or substituted heterocycle is substituted with one or more of:

1) $C_{1-8}$ alkyl, $C_{2-8}$ alkenyl or $C_{2-8}$ alkynyl, unsubstituted or substituted with:
   a) $C_{1-4}$ alkoxy,
   b) NR$^6$R$^7$,
   c) $C_{3-6}$ cycloalkyl,
   d) aryl or heterocycle,
   e) HO,
   f) —S(O)$_m$R$^4$,
   g) —C(O)NR$^6$R$^7$, or
   h) $C_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

provided that $Z^1$ is not selected from piperazinyl, oxopiperazinyl, dioxopiperazinyl, piperidinyl, oxopiperidinyl or pyrrolidinyl;

$Z^2$ is selected from a bond, unsubstituted or substituted aryl and unsubstituted or substituted heteroaryl, wherein the substituted aryl or substituted heteroaryl is substituted with one or more of:

1) $C_{1-8}$ alkyl, $C_{2-8}$ alkenyl or $C_{2-8}$ alkynyl, unsubstituted or substituted with:
   a) $C_{1-4}$ alkoxy,
   b) NR$^6$R$^7$,
   c) $C_{3-6}$ cycloalkyl,
   d) aryl or heterocycle,
   e) HO,
   f) —S(O)$_m$R$^4$,
   g) —C(O)NR$^6$R$^7$, or
   h) $C_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

provided that $Z^2$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 1, 2, 3, 4, 5, 6 or 7; and
v is 2 to 6;

or a pharmaceutically acceptable salt or stereoisomer thereof.

In a second embodiment of this invention, the inhibitors of prenyl-protein transferase are illustrated by the formula A:

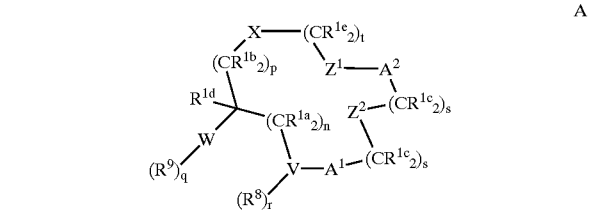

wherein:

$R^{1a}$, $R^{1b}$, $R^{1c}$, $R^{1d}$ and $R^{1e}$ are independently selected from:
  a) hydrogen,
  b) aryl, heterocycle, $C_3$–$C_{10}$ cycloalkyl, $R^{10}$O—, $R^{11}$S(O)$_m$—, $R^{10}$C(O)NR$^{10}$—, (R$^{10}$)$_2$N—C(O)—, CN, NO$_2$, (R$^{10}$)$_2$N—C(NR$^{10}$)—, (R$^{10}$)$_2$N—C(O)NR$^{10}$—, $R^{10}$C(O)—, $R^{10}$OC(O)—, —N(R$^{10}$)$_2$, or $R^{11}$OC(O)NR$^{10}$—,
  c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)NR$^{10}$—, (R$^{10}$)$_2$N—C(O)—, CN, (R$^{10}$)$_2$N—C(NR$^{10}$)—, $R^{10}$C(O)—, $R^{10}$OC(O)—, —N(R$^{10}$)$_2$, and $R^{11}$OC(O)—NR$^{10}$—;

or two $R^{1e}$s, on the same carbon atom may be combined to form —(CH$_2$)$_v$— wherein one of the CH$_2$ moieties is optionally replaced with —C(=O)—, —NH— or —NHC(=O)—; $R^4$ is selected from $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO,
  e)

$$\underset{O}{\overset{}{\underset{\|}{\text{C}}}}\!\!-\!\!R^{11},$$

f) —SO$_2$R$^{11}$ or
  g) N(R$^{10}$)$_2$;
$R^6$ and $R^7$ are independently selected from H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e)

$$\underset{O}{\overset{}{\underset{\|}{\text{C}}}}\!\!-\!\!R^{11},$$

f) —SO$_2$R$^{11}$, or
  g) N(R$^{10}$)$_2$, or
$R^6$ and $R^7$ may be joined in a ring;
$R^8$ is independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, —N(R$^{10}$)$_2$, or R$^{11}$OC(O)NR$^{10}$—, and
  c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, —N(R$^{10}$)$_2$, or R$^{10}$OC(O)NH—;
$R^9$ is selected from:
  a) hydrogen,
  b) $C_2$–$C_6$ alkenyl, $C_2$–$C_6$ alkynyl, $C_1$–$C_6$ perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, —N(R$^{10}$)$_2$, or R$^{11}$OC(O)NR$^{10}$—, and
  c) $C_1$–$C_6$ alkyl unsubstituted or substituted by $C_1$–$C_6$ perfluoroalkyl, F, Cl, Br, R$^{10}$O—, R$^{11}$S(O)$_m$—, CN, R$^{10}$C(O)NR$^{10}$—, (R$^{10}$)$_2$NC(O)—, R$^{10}$$_2$N—C(NR$^{10}$)—, R$^{10}$C(O)—, R$^{10}$OC(O)—, —N(R$^{10}$)$_2$ or R$^{11}$OC(O)NR$^{10}$—;
$R^{10}$ is independently selected from hydrogen, $C_1$–$C_6$ alkyl, benzyl, unsubstituted or substituted aryl and unsubstituted or substituted heterocycle;
$R^{11}$ is independently selected from $C_1$–$C_6$ alkyl unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;
$A^1$ is selected from a bond, —N(R$^{10}$)—, S(O)$_m$ and O;
$A^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, —NR$^1$OC(O)NR$^{10}$—, S(O)$_m$ and —C(R$^{1c}$)$_2$—;
W is heteroaryl;
V is selected from:
  a) heteroaryl, and
  b) aryl;
X is selected from —C(O)—, —C(O)NR$^{10}$—, —NR$^{10}$C(O)—, —NR$^{10}$C(O)—O—, —O—C(O)NR$^{10}$—, —NROC(O)NR$^{10}$—, O, —N(R$^{10}$)—, —S(O)$_2$N(R$^{10}$)—, —N(R$^{11}$)S(O)$_2$— and S(O)$_m$;
$Z^1$ is selected from unsubstituted or substituted aryl and unsubstituted or substituted heteroaryl, wherein the substituted aryl or substituted heteroaryl is substituted with one or more of:
  1) $C_{1-4}$ alkyl, unsubstituted or substituted with:
    a) $C_{1-4}$ alkoxy,
    b) NR$^6$R$^7$,
    c) $C_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) $C_3$–$C_6$ cycloalkyl;
provided that $Z^1$ is not selected from piperazinyl, oxopiperazinyl, dioxopiperazinyl, piperidinyl, oxopiperidinyl or pyrrolidinyl;
$Z^2$ is selected from a bond, unsubstituted or substituted aryl and unsubstituted or substituted heteroaryl, wherein the substituted aryl or substituted heteroaryl is substituted with one or more of:
  1) $C_{1-4}$ alkyl, unsubstituted or substituted with:
    a) $C_{1-4}$ alkoxy,
    b) NR$^6$R$^7$,
    c) $C_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$, 9) —S(O)$_m$R$^4$,
10) —C(O)NR$^6$R$^7$, or
11) C$_3$–C$_6$ cycloalkyl;

provided that Z$^2$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3, 4, 5, 6 or 7;

or a pharmaceutically acceptable salt or stereoisomer thereof.

In a third embodiment of this invention, the inhibitors of prenyl-protein transferase are illustrated by the formula A:

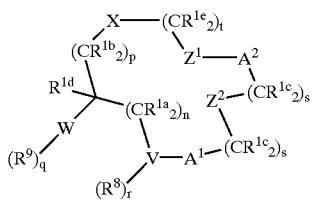

A wherein:

R$^{1a}$, R$^{1b}$ and R$^{1c}$ are independently selected from hydrogen and C$_1$–C$_6$ alkyl;

R$^{1d}$ and R$^{1e}$ are independently selected from:
  a) hydrogen,
  b) aryl, heterocycle, C$_3$–C$_{10}$ cycloalkyl, R$^{10}$O— or —N(R$^{10}$)$_2$, and
  c) unsubstituted or substituted C$_1$–C$_6$ alkyl, unsubstituted or substituted C$_2$–C$_6$ alkenyl or unsubstituted or substituted C$_2$–C$_6$ alkynyl, wherein the substituent on the substituted C$_1$–C$_6$ alkyl, substituted C$_2$–C$_6$ alkenyl or substituted C$_2$–C$_6$ alkynyl is selected from: unsubstituted or substituted aryl, heterocycle, C$_3$–C$_{10}$ cycloalkyl, C$_2$–C$_6$ alkenyl, R$^{10}$O— and —N(R$^{10}$)$_2$;

or two R$^{1e}$s, on the same carbon atom may be combined to form —(CH$_2$)$_v$—, wherein one of the CH$_2$ moieties is optionally replaced with —C(=O)—, —NH— or —NHC(=O)—;

R$^4$ is selected from C$_{1-4}$ alkyl and C$_{3-6}$ cycloalkyl, unsubstituted or substituted with:
  a) C$_{1-4}$ alkoxy,
  b) halogen, or
  c) aryl or heterocycle;

R$^6$ and R$^7$ are independently selected from H; C$_{1-4}$ alkyl, C$_{3-6}$ cycloalkyl, aryl and heterocycle, unsubstituted or substituted with:
  a) C$_{1-4}$ alkoxy,
  b) halogen, or
  c) aryl or heterocycle;

R$^8$ is independently selected from:
  a) hydrogen,
  b) unsubstituted or substituted aryl, unsubstituted or substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by: unsubstituted or substituted aryl, unsubstituted or substituted heterocycle, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^9$ is selected from:
  a) hydrogen,
  b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, —N(R$^{10}$)$_2$, or R$^{11}$OC(O)NR$^{10}$—;

R$^{10}$ is independently selected from hydrogen, C$_1$–C$_6$ alkyl, benzyl, unsubstituted or substituted aryl and unsubstituted or substituted heterocycle;

R$^{11}$ is independently selected from C$_1$–C$_6$ alkyl, unsubstituted or substituted aryl and unsubstituted or substituted heterocycle;

R$^{12}$ is independently selected from hydrogen, C$_1$–C$_6$ alkyl, C$_1$–C$_3$ perfluoroalkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

A$^1$ is selected from a bond, —N(R$^{10}$)—, S(O)$_m$ and 0;
A$^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, S(O)$_m$ and —C(R$^{1c}$)$_2$—;

V is selected from:
  a) heterocycle selected from pyridinyl, pyridonyl, 2-oxopiperidinyl, indolyl, quinolinyl and isoquinolinyl, and
  b) aryl;

W is a heterocycle selected from imidazolyl, pyridinyl, and triazolyl;

X and Y are independently selected from —C(O)—, —C(O)NR$^{10}$—, —NR$^{10}$C(O)—, —NR$^{10}$C(O)NR$^{10}$—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted aryl or unsubstituted or substituted heteroaryl, wherein the substituted aryl or substituted heteroaryl is independently substituted with one or two of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;

provided that Z$^1$ is not selected from piperazinyl, oxopiperazinyl, dioxopiperazinyl, piperidinyl, oxopiperidinyl or pyrrolidinyl;

$Z^2$ is selected from a bond, unsubstituted or substituted aryl and unsubstituted or substituted heteroaryl, wherein the substituted aryl or substituted heteroaryl is substituted independently with one or two of:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) $-S(O)_mR^4$, or
   g) $-C(O)NR^6R^7$,
2) aryl or heterocycle,
3) halogen,
4) $OR^6$,
5) $NR^6R^7$,
6) CN,
7) $NO_2$,
8) $CF_3$,
9) $-S(O)_mR^4$,
10) $-C(O)NR^6R^7$, or
11) $C_3-C_6$ cycloalkyl;

provided that $Z^2$ is not selected from piperazinyl, oxopiperazinyl, dioxopiperazinyl, piperidinyl, oxopiperidinyl or pyrrolidinyl;
m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
t is 1, 2, 3, 4, 5, 6 or 7;
or a pharmaceutically acceptable salt or stereoisomer thereof In a fourth embodiment of this invention, the inhibitors of prenyl-protein transferase are illustrated by the formula B:

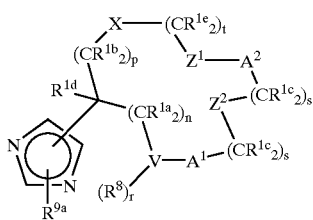

B wherein:
$R^{1a}$, $R^{1b}$ and $R^{1c}$ are independently selected from:
a) hydrogen,
b) aryl, heterocycle, cycloalkyl, $R^{10}O-$, $-N(R^{10})_2$ or $C_2-C_6$ alkenyl, and
c) $C_1-C_6$ alkyl unsubstituted or substituted by aryl, heterocycle, $C_3-C_{10}$ cycloalkyl, $C_2-C_6$ alkenyl, $R^{10}O-$, or $-N(R^{10})_2$;

$R^{1d}$ and $R^{1e}$ are independently selected from:
a) hydrogen,
b) unsubstituted or substituted aryl, unsubstituted or substituted heterocycle, $C_3-C_{10}$ cycloalkyl, $R^{10}O-$, $R^{11}S(O)_m-$, $R^{10}C(O)NR^{10}-$, $(R^{10})_2N-C(O)-$, CN, $NO_2$, $(R^{10})_2N-C(NR^{10})-$, $(R^{10})_2N-C(O)NR^{10}-$, $R^{10}C(O)-$, $R^{10}C(O)-$, $-N(R^{10})_2$, or $R^{11}OC(O)NR^{10}-$,
c) unsubstituted or substituted $C_1-C_6$ alkyl, unsubstituted or substituted $C_2-C_6$ alkenyl or unsubstituted or substituted $C_2-C_6$ alkynyl, wherein the substituent on the substituted $C_1-C_6$ alkyl, substituted $C_2-C_6$ alkenyl or substituted $C_2-C_6$ alkynyl is selected from: unsubstituted or substituted aryl, heterocyclic, $C_3-C_{10}$ cycloalkyl, $C_2-C_6$ alkenyl, $C_2-C_6$ alkynyl, $C_1-C_6$ perfluoroalkyl, halogen, $R^{10}O-$, $R^4S(O)_m-$, $R^4S(O)_2NR^{10}-$, $R^{10}C(O)NR^{10}-$, $(R^{10})_2N-C(O)-$, CN, $(R^{10})_2N-C(NR^{10})-$, $R^{10}C(O)-$, $R^{10}OC(O)-$, $-N(R^{10})_2$, and $R^{10}OC(O)-NR^{10}-$;

or two $R^{1e}$s, on the same carbon atom may be combined to form $-(CH_2)_v-$, wherein one of the $CH_2$ moieties is optionally replaced with $-C(=O)-$, $-NH-$ or $-NHC(=O)-$;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO,
e)

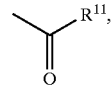

f) $-SO_2R^{11}$
g) $N(R^{10})_2$, or
h) $C_{3-6}$ cycloalkyl;

$R^8$ is independently selected from:
a) hydrogen,
b) unsubstituted or substituted aryl, $C_1-C_6$ alkyl, $C_2-C_6$ alkenyl, $C_2-C_6$ alkynyl, $C_1-C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1-C_6$ alkyl substituted by: unsubstituted or substituted aryl, $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is selected from hydrogen, $C_1-C_6$ alkyl and $C_1-C_6$ perfluoroalkyl,
$R^{10}$ is independently selected from hydrogen, $C_1-C_6$ alkyl, benzyl and unsubstituted or substituted aryl;
$R^{11}$ is independently selected from $C_1-C_6$ alkyl and unsubstituted or substituted aryl;
$R^{12}$ is independently selected from hydrogen, $C_1-C_6$ alkyl, unsubstituted or substituted benzyl, unsubstituted or substituted aryl, unsubstituted or substituted heterocycle, and $C_1-C_6$ alkyl substituted with unsubstituted or substituted aryl or unsubstituted or substituted heterocycle;
$A^1$ is selected from a bond, $-N(R^{10})-$, $S(O)_m$ and O;
$A^2$ is selected from a bond, $-C(O)-$, $-C(O)NR^{10}-$, $-NR^{10}C(O)-$, O, $-N(R^{10})-$, $-S(O)_2N(R^{10})-$, $-N(R^{11})S(O)_2-$, $S(O)_m$ and $-C(R^{1c})_2-$;
V is selected from:
a) heterocycle selected from pyridinyl, pyridonyl, 2-oxopiperidinyl, indolyl, quinolinyl and isoquinolinyl, and
b) aryl;

X is selected from —C(O)—, —C(O)NR$^{10}$—, —NR$^{10}$C(O)—, —NR$^{10}$C(O)NR$^{10}$—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted aryl or unsubstituted or substituted heterocycle, wherein the substituted aryl or substituted heterocycle is independently substituted with one or two of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$, or
   h) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;
provided that Z$^1$ is not selected from piperazinyl, oxopiperazinyl, dioxopiperazinyl, piperidinyl, oxopiperidinyl or pyrrolidinyl;

Z$^2$ is selected from a bond, unsubstituted or substituted aryl and unsubstituted or substituted heteroaryl, wherein the substituted aryl or substituted heteroaryl is substituted with one or more of:
1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$,
   g) —C(O)NR$^6$R$^7$, or
   h) C$_{1-4}$perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;
provided that Z$^2$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4;
r is 0 to 5;
s is 0, 1, 2 or 3; and
t is 1, 2, 3, 4, 5, 6 or 7;
or a pharmaceutically acceptable salt or stereoisomer thereof.

In a fifth embodiment of this invention, the inhibitors of prenyl-protein transferase are illustrated by the formula B:

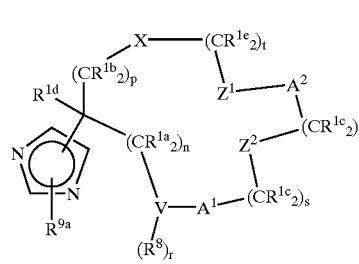

wherein:
R$^{1a}$, R$^{1b}$ and R$^{1c}$ are independently selected from hydrogen or C$_1$–C$_6$ alkyl;
R$^{1d}$ and R$^{1e}$ are independently selected from:
   a) hydrogen,
   b) aryl, heterocycle, C$_3$–C$_{10}$ cycloalkyl, R$^{10}$O— or —N(R$^{10}$)$_2$, and
   c) C$_1$–C$_6$ alkyl, C$_2$–C$_6$ alkenyl or C$_2$–C$_6$ alkynyl, unsubstituted or substituted by aryl, heterocycle, C$_3$–C$_{10}$ cycloalkyl, C$_2$–C$_6$ alkenyl, R$^{10}$O—, or —N(R$^{10}$)$_2$;
or two R$^{1e}$s on the same carbon atom may be combined to form —(CH$_2$)$_v$—, wherein one of the CH$_2$ moieties is optionally replaced with —C(=O)—, —NH— or —NHC(=O)—;

R$^4$ is selected from C$_{1-4}$ alkyl and C$_{3-6}$ cycloalkyl, unsubstituted or substituted with:
   a) C$_{1-4}$ alkoxy,
   b) halogen, or
   c) aryl or heterocycle;
R$^6$ and R$^7$ are independently selected from:
   a) hydrogen,
   b) C$_1$–C$_6$ alkyl, C$_2$–C$_6$ alkenyl, C$_2$–C$_6$ alkynyl, R$^{10}$C(O)— or R$^{10}$OC(O)— and
   c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;
R$^8$ is independently selected from:
   a) hydrogen,
   b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
   c) C$_1$–C$_6$ alkyl substituted by: unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$), R$^{10}$C(O)—, —N(R$^{10}$)$_2$, or R$^1$OC(O)NR$^{10}$—;
R$^{9a}$ is selected from hydrogen, C$_1$–C$_6$ alkyl and C$_1$–C$_6$ perfluoroalkyl;
R$^{10}$ is independently selected from hydrogen, C$_1$–C$_6$ alkyl, benzyl and unsubstituted or substituted aryl;
R$^{11}$ is independently selected from C$_1$–C$_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is selected from a bond, —N($R^{10}$)—, S(O)$_m$ and O;

$A^2$ is selected from a bond, —C(O)—, —C(O)N$R^{10}$—, —N$R^{10}$C(O)—, O, —N($R^{10}$)—, —S(O)$_2$N($R^{10}$)—, —N($R^{10}$)S(O)$_2$—, S(O)$_m$ and —C($R^{1c}$)$_2$—;

V is selected from:
  a) heteroaryl selected from imidazolyl, pyridinyl, thiazolyl, indolyl, quinolinyl, isoquinolinyl, and thienyl, and
  b) aryl;

X is selected from —C(O)—, —C(O)N$R^{10}$—, —N$R^{10}$C(O)—, —N$R^{10}$C(O)N$R^{10}$—, O, —N($R^{10}$)—, —S(O)$_2$N($R^{10}$)—, —N($R^{10}$)S(O)$_2$—, and S(O)$_m$;

$Z^1$ is selected from unsubstituted or substituted aryl or unsubstituted or substituted heteroaryl, wherein the substituted aryl or substituted heteroaryl is independently substituted with one or two of:
  1) $C_{1-4}$ alkyl, unsubstituted or substituted with:
    a) $C_{1-4}$ alkoxy,
    b) N$R^6R^7$,
    c) $C_{3-6}$ cycloalkyl,
    d) aryl or heterocycle,
    e) HO,
    f) —S(O)$_m$$R^4$, or
    g) —C(O)N$R^6R^7$,
  2) aryl or heterocycle,
  3) halogen,
  4) O$R^6$,
  5) N$R^6R^7$,
  6) CN,
  7) NO$_2$,
  8) CF$_3$,
  9) —S(O)$_m$$R^4$,
  10) —C(O)N$R^6R^7$, or
  11) $C_3$–$C_6$ cycloalkyl;

provided that $Z^1$ is not selected from piperazinyl, oxopiperazinyl, dioxopiperazinyl, piperidinyl, oxopiperidinyl or pyrrolidinyl;

$Z^2$ is selected from a bond, unsubstituted or substituted aryl and unsubstituted or substituted heteroaryl, wherein the substituted aryl or substituted heteroaryl is substituted with one or more of:
  1) $C_{1-8}$ alkyl, $C_{2-8}$ alkenyl or $C_{2-8}$ alkynyl, unsubstituted or substituted with:
    a) $C_{1-4}$ alkoxy,
    b) N$R^6R^7$,
    c) $C_{3-6}$ cycloalkyl,
    d) aryl or heterocycle,
    e) HO,
    f) —S(O)$_m$$R^4$,
    g) —C(O)N$R^6R^7$, or
    h) $C_{1-4}$ perfluoroalkyl;
  2) substituted or unsubstituted aryl or substituted or unsubstituted heterocycle,
  3) halogen,
  4) O$R^6$,
  5) N$R^6R^7$,
  6) CN,
  7) NO$_2$,
  8) CF$_3$,
  9) —S(O)$_m$$R^4$,
  10) —OS(O)$_2$$R^4$,
  11) —C(O)N$R^6R^7$,
  12) —C(O)O$R^6$, or
  13) $C_3$–$C_6$ cycloalkyl;

provided that $Z^2$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3, 4, 5, 6 or 7;

or a pharmaceutically acceptable salt or stereoisomer thereof.

Another embodiment of the compounds of this invention is illustrated by the formula C:

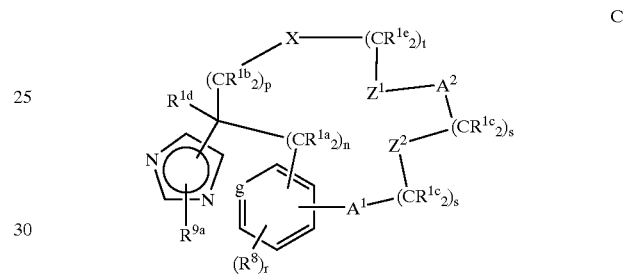

wherein:
g is CH or N;
$R^{1a}$, $R^{1b}$ and $R^{1c}$ are independently selected from hydrogen or $C_1$–$C_6$ alkyl;
$R^{1d}$ and $R^{1e}$ are independently selected from:
  a) hydrogen,
  b) aryl, heterocycle, $C_3$–$C_{10}$ cycloalkyl, $R^{10}$O— or —N($R^{10}$)$_2$, and
  c) $C_1$–$C_6$ alkyl, $C_2$–$C_6$ alkenyl or $C_2$–$C_6$ alkynyl, unsubstituted or substituted by aryl, heterocycle, $C_3$–$C_{10}$ cycloalkyl, $C_2$–$C_6$ alkenyl, $R^{10}$O—, or —N($R^{10}$)$_2$;

or two $R^{1e}$s on the same carbon atom may be combined to form —(CH$_2$)$_v$—, wherein one of the CH$_2$ moieties is optionally replaced with —C(=O)—, —NH— or —NHC(=O)—;

$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^6$ and $R^7$ are independently selected from:
  a) hydrogen,
  b) $C_1$–$C_6$ alkyl, $C_2$–$C_6$ alkenyl, $C_2$–$C_6$ alkynyl, $R^{10}$C(O)— or $R^{10}$OC(O)— and
  c) $C_1$–$C_6$ alkyl substituted by $C_1$–$C_6$ perfluoroalkyl, $R^{10}$O—, $R^{10}$C(O)N$R^{10}$—, ($R^{10}$)$_2$N—C(N$R^{10}$)—, $R^{10}$C(O)—, $R^{10}$C(O)—, —N($R^{10}$)$_2$, or $R^{11}$OC(O)N$R^{10}$—;

$R^8$ is independently selected from:
  a) hydrogen,
  b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O-$, $R^{10}C(O)NR^{10}-$, CN, NO$_2$, $(R^{10})_2N-C(NR^{10})-$, $R^{10}C(O)-$, $-N(R^{10})_2$, or $R^{11}OC(O)NR^{10}-$, and c) C$_1$–C$_6$ alkyl substituted by unsubstituted or substituted aryl, C$_1$–C$_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is selected from hydrogen, C$_1$–C$_6$ alkyl and C$_1$–C$_6$ perfluoroalkyl;

$R^{10}$ is independently selected from hydrogen, C$_1$–C$_6$ alkyl, benzyl and unsubstituted or substituted aryl;

$R^{11}$ is independently selected from C$_1$–C$_6$ alkyl and unsubstituted or substituted aryl;

$R^{12}$ is independently selected from hydrogen, C$_1$–C$_6$ alkyl, C$_1$–C$_3$ perfluoroalkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

A$^1$ is selected from a bond, $-N(R^{10})-$, $S(O)_m$ and O;

A$^2$ is selected from a bond, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, $S(O)_m$ and $-C(R^{1c})_2-$;

X is selected from: $-C(O)-$, $-C(O)NR^{10}-$, $-NR^{10}C(O)-$, $-NR^{10}C(O)NR^{10}-$, O, $N(R^{10})-$, $-S(O)_2N(R^{10})-$, $-N(R^{11})S(O)_2-$, and $S(O)_m$;

Z$^1$ is selected from unsubstituted or substituted aryl or unsubstituted or substituted heteroaryl, wherein the substituted aryl or substituted heteroaryl is substituted with one or two of:

1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) $-S(O)_mR^4$, or
   g) $-C(O)NR^6R^7$,
2) aryl or heterocycle,
3) halogen,
4) OR$^6$,
5) NR$^6$R$^7$,
6) CN,
7) NO$_2$,
8) CF$_3$,
9) $-S(O)_mR^4$,
10) $-C(O)NR^6R^7$, or
11) C$_3$–C$_6$ cycloalkyl;

provided that Z$^1$ is not selected from piperazinyl, oxopiperazinyl, dioxopiperazinyl, piperidinyl, oxopiperidinyl or pyrrolidinyl;

Z$^2$ is selected from a bond, unsubstituted or substituted aryl and unsubstituted or substituted heteroaryl, wherein the substituted aryl or substituted heteroaryl is substituted with one or more of:

1) C$_{1-8}$ alkyl, C$_{2-8}$ alkenyl or C$_{2-8}$ alkynyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) $-S(O)_mR^4$,
   g) $-C(O)NR^6R^7$, or
   h) C$_{1-4}$perfluoroalkyl;

2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) $-S(O)_mR^4$,
10) $-OS(O)_2R^4$,
11) $-C(O)NR^6R^7$,
12) $-C(O)OR^6$, or
13) C$_3$–C$_6$ cycloalkyl;

provided that Z$^2$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3, 4, 5, 6 or 7;

or a pharmaceutically acceptable salt or stereoisomer thereof.

In another embodiment of this invention, the inhibitors of prenyl-protein transferase are illustrated by the formula D:

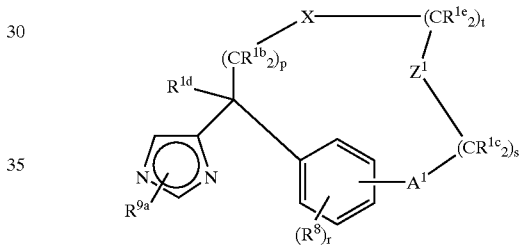

wherein:

$R^{1b}$ and $R^1c$ are independently selected from hydrogen or C$_1$–C$_6$ alkyl;

$R^{1d}$ and $R^1e$ are independently selected from:
   a) hydrogen,
   b) aryl, heterocycle, C$_3$–C$_{10}$ cycloalkyl, $R^{10}O-$ or $-N(R^{10})$, and
   c) C$_1$–C$_6$ alkyl, C$_2$–C$_6$ alkenyl or C$_2$–C$_6$ alkynyl, unsubstituted or substituted by aryl, heterocycle, C$_3$–C$_{10}$ cycloalkyl, C$_2$–C$_6$ alkenyl, $R^{10}O-$, or $-N(R^{10})_2$;

or two R$^{1e}$s on the same carbon atom may be combined to form $-(CH_2)_v-$, wherein one of the CH$_2$ moieties is optionally replaced with $-C(=O)-$, $-NH-$ or $-NHC(=O)-$;

R$^4$ is selected from C$_{1-4}$ alkyl and C$_{3-6}$ cycloalkyl, unsubstituted or substituted with:
   a) C$_{1-4}$ alkoxy,
   b) halogen, or
   c) aryl or heterocycle;

R$^6$ and R$^7$ are independently selected from:
   a) hydrogen,
   b) C$_1$–C$_6$ alkyl, C$_2$–C$_6$ alkenyl, C$_2$–C$_6$ alkynyl, $R^{10}C(O)-$ or $R^{10}OC(O)-$ and
   c) C$_1$–C$_6$ alkyl substituted by C$_1$–C$_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^8$ is independently selected from:
 a) hydrogen,
 b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—C$(NR^{10})$—, $R^{10}C(O)$—, —$N(R^{10})_2$, or $R^{11}OC(O)NR^{10}$—, and
 c) $C_1$–$C_6$ alkyl substituted by unsubstituted or substituted aryl, $C_1$–$C_6$ perfluoroalkyl, $R^{10}O$, $R^{10}C(O)NR^{10}$—, $(R^{10})_2N$—C$(NR^{10})$—, $R^{10}C(O)$—, —$N(R^{10})_2$, or $R^{11}OC(O)NR^{10}$—;

$R^{9a}$ is selected from hydrogen, $C_1$–$C_6$ alkyl and $C_1$–$C_6$ perfluoroalkyl;

$R^{10}$ and $R^{12}$ are independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —$N(R^{10})$—, $S(O)_m$ and O;

X is selected from: —C(O)—, —C(O)$NR^{10}$—, —$NR^{10}$C(O)—, —$NR^{10}$C(O)$NR^{10}$—, O, —$N(R^{10})$—, —$S(O)_2$N$(R^{10})$—, —$N(R^{10})S(O)_2$—, and $S(O)_m$;

$Z^1$ is selected from unsubstituted or substituted aryl or unsubstituted or substituted heteroaryl, wherein the substituted aryl or substituted heteroaryl is substituted with one or two of:
 1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$, or
   g) —$C(O)NR^6R^7$,
 2) aryl or heterocycle,
 3) halogen,
 4) $OR^6$,
 5) $NR^6R^7$,
 6) CN,
 7) $NO_2$,
 8) $CF_3$,
 9) —$S(O)_mR^4$,
 10) —$C(O)NR^6R^7$, or
 11) $C_3$–$C_6$ cycloalkyl;
provided that $Z^1$ is not selected from piperazinyl, oxopiperazinyl, dioxopiperazinyl, piperidinyl, oxopiperidinyl or pyrrolidinyl;
m is 0, 1 or 2;
n is 0, 1, 2, 3 or 4;
p is 0, 1, 2, 3 or 4;
r is 0 to 5;
s is independently 0, 1, 2 or 3; and
t is 1, 2, 3, 4, 5, 6 or 7;
or a pharmaceutically acceptable salt or stereoisomer thereof.

In another embodiment of this invention, the inhibitors of prenyl-protein transferase are illustrated by the formula E:

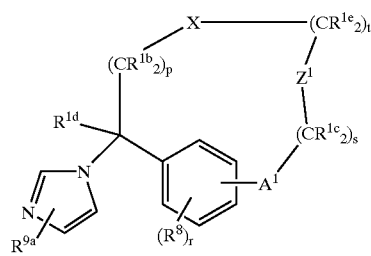

wherein:
$R^{1b}$ and $R^{1c}$ are independently selected from hydrogen or $C_1$–$C_6$ alkyl;
$R^{1d}$ is selected from:
 a) hydrogen,
 b) aryl, heterocycle or $C_3$–$C_{10}$ cycloalkyl, and
 c) $C_1$–$C_6$ alkyl, $C_2$–$C_6$ alkenyl or $C_2$–$C_6$ alkynyl, unsubstituted or substituted by aryl, heterocycle, $C_3$–$C_{10}$ cycloalkyl, $C_2$–$C_6$ alkenyl, $R^{10}O$—, or —$N(R^{10})_2$;

$R^{1e}$ is independently selected from:
 a) hydrogen,
 b) aryl, heterocycle, $C_3$–$C_{10}$ cycloalkyl, $R^{10}O$—, —$N(R^{10})_2$ or $C_2$–$C_6$ alkenyl, and
 c) $C_1$–$C_6$ alkyl, $C_2$–$C_6$ alkenyl or $C_2$–$C_6$ alkynyl, unsubstituted or substituted by aryl, heterocycle, $C_3$–$C_{10}$ cycloalkyl, $C_2$–$C_6$ alkenyl, $R^{10}O$—, or —$N(R^{10})_2$;
or two $R^{1e}$s on the same carbon atom may be combined to form —$(CH_2)_v$—, wherein one of the $CH_2$ moieties is optionally replaced with —C(=O)—, —NH— or —NHC(=O)—;

$R^4$ is selected from $C_{1-4}$ alkyl and $C_{3-6}$ cycloalkyl, unsubstituted or substituted with:
 a) $C_{1-4}$ alkoxy,
 b) halogen, or
 c) aryl or heterocycle;

$R^6$ and $R^7$ are independently selected from:
 a) hydrogen,
 b) $C_1$–$C_6$ alkyl, $C_2$–$C_6$ alkenyl, $C_2$–$C_6$ alkynyl, $R^{10}C(O)$— or $R^{10}OC(O)$— and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is independently selected from:
 a) hydrogen,
 b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—C$(NR^{10})$—, $R^{10}C(O)$—, —$N(R^{10})_2$, or $R^{11}OC(O)NR^{10}$—, and
 c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—C$(NR^{10})$—, $R^{10}C(O)$—, —$N(R^{10})_2$, or $R^{11}OC(O)NR^{10}$—;

$R^{9a}$ is selected from hydrogen, $C_1$–$C_6$ alkyl and $C_1$–$C_6$ perfluoroalkyl;

$R^{10}$ and $R^{12}$ are independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —$N(R^{10})$—, $S(O)_m$ and O;

X is selected from —C(O)—, —C(O)NR$^{10}$—, —NR$^{10}$C(O)—, —NR$^{10}$C(O)NR$^{10}$—, O, —N(R$^{10}$)—, —S(O)$_2$N(R$^{10}$)—, —N(R$^{10}$)S(O)$_2$—, and S(O)$_m$;

Z$^1$ is selected from unsubstituted or substituted aryl or unsubstituted or substituted heteroaryl, wherein the substituted aryl or substituted heteroaryl is substituted with one or two of:
1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) C$_3$–C$_6$ cycloalkyl;
provided that Z$^1$ is not selected from piperazinyl, oxopiperazinyl, dioxopiperazinyl, piperidinyl, oxopiperidinyl or pyrrolidinyl;

m is 0, 1 or 2;
n is 0, 1, 2, 3 or 4;
p is 0, 1, 2, 3 or 4; provided p is 1, 2, 3 or 4 when X is —NR$^{10}$C(O)—, —NR$^{10}$C(O)NR$^{10}$—, O, —N(R$^{10}$)— or N(R$^{10}$)S(O)$_2$—;
r is 0 to 5;
s is independently 0, 1, 2 or 3; and
t is 1, 2, 3, 4, 5, 6 or 7;
or a pharmaceutically acceptable salt or stereoisomer thereof.

Examples of the compounds of the invention are:
5-(4-Cyano-8-methyl-10-oxo-2-oxa-9-aza-tricyclo[11.3.1.1$^{3,7}$]octadeca-1(16),3(18),4,6,13(17),14-hexaen-8-yl)-1-methyl-1H-imidazol-1-ium 2,2,2-trifluoroacetate;
5-(4-Cyano-8-methyl-10-oxo-2-oxa-9-aza-tricyclo[13.3.1.1$^{3,7}$]eicosa-1(18),3(20),4,6,15(19),16-hexaen-8-yl)-1-methyl-1H-imidazol-1-ium 2,2,2-trifluoroacetate;
5-(4-Cyano-8-methyl-10-oxo-2-oxa-9-aza-tricyclo[15.3.1.1$^{3,7}$]docosa-1(20),3(22),4,6,17(21),18-hexaen-8-yl)-1-methyl-1H-imidazol-1-ium 2,2,2-trifluoroacetate;
5-(4-Cyano-8-methyl-10-oxo-2-oxa-9-aza-(16-spiro-(2-cyclohexanone) tricyclo[15.3.1.1$^{3,7}$]docosa-1(20),3(22),4,6,17(21),18-hexaen-8-yl)-1-methyl-1H-imidazol-1-ium 2,2,2-trifluoroacetate;
14-Amino-14-(3-methyl-3H-imidazol-4-yl)-2,9-dioxa-tricyclo[13.3.1.1$^{3,7}$]eicosa-1(18),3,5,7(20),15(19),16-hexaene-18-carbonitrile;
15-Amino-15-(3-methyl-3H-imidazol-4-yl)-2,9-dioxa-tricyclo[14.3.1.1$^{3,7}$]heneicosa-1(20),3,5,7(21), 16.18-hexaene-19-carbonitrile;
14-amino-14-(3-methyl-3H-imidazol-4-yl)-2-oxa-10-aza-tricyclo[13.3.1.1$^{3,7}$]eicosa-1(18),3,5,7(20),15(19),16-hexaene-18-carbonitrile
or the free bases, the pharmaceutically acceptable salts or stereoisomers thereof.

Specific example of the compounds of the instant invention include:

14-Amino-14-(3-methyl-3H-imidazol-4-yl)-2,9-dioxa-tricyclo [13.3.1.1$^{3,7}$]eicosa-1(18),3,5,7(20),15(19),16-hexaene-18-carbonitrile;

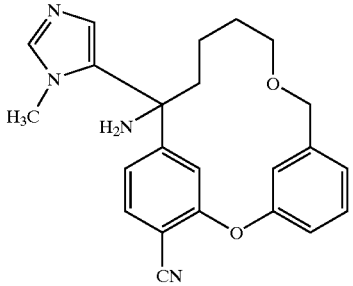

or a pharmaceutically acceptable salt or stereoisomer thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119–1190) When any variable (e.g. aryl, heterocycle, R$^{1a}$, R$^6$ etc.) occurs more than one time in any constituent, its definition on each occurrence is independent at every other occurrence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is C$_2$–C$_6$ alkenyl.
Preferably, alkynyl is C$_2$–C$_6$ alkynyl.

As used herein, "cycloalkyl" is intended to include cyclic saturated aliphatic hydrocarbon groups having the specified number of carbon atoms. Preferably, cycloalkyl is C$_3$–C$_{10}$ cycloalkyl. Examples of such cycloalkyl elements include, but are not limited to, cyclopropyl, cyclobutyl, cyclopentyl, cyclohexyl and cycloheptyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic, as used herein, includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, CF3, NH2, N(C1–C6 alkyl)2, NO2, CN, (C1–C6 alkyl)O—, (aryl)O—, —OH, (C1–C6 alkyl)S(O)m—, (C1–C6 alkyl)C(O)NH—, H2N—C(NH)—, (C1–C6 alkyl)C(O)—, (C1–C6 alkyl)OC(O)—, N3,(C1–C6 alkyl)OC(O)NH—, phenyl, pyridyl, imidazolyl, oxazolyl, isoxazolyl, thiazolyl, thienyl, furyl, isothiazolyl and C1–C20 alkyl.

Preferably, as used herein in the definition of $R^6$ and $R^7$, the substituted $C_{1-6}$ alkyl, substituted $C_{2-6}$ alkenyl, substituted $C_{2-6}$ alkynyl, substituted $C_{3-6}$ cycloalkyl, substituted aroyl, substituted aryl, substituted heteroaroyl, substituted arylsulfonyl, substituted heteroarylsulfonyl, substituted heterocycle and substituted $C_{6-10}$ multicyclic alkyl ring, include moieties containing from 1 to 3 substituents in addition to the point of attachment to the rest of the compound.

The moiety formed when, in the definition of $R^{1a}$, $R^{1b}$, $R^{1c}$, $R^{1d}$ and $R^{1e}$, two $R^{1a}$s, two $R^{1b}$s, two $R^{1c}$s, two $R^{1d}$s or two $R^{1e}$s, on the same carbon atom are combined to form —(CH$_2$)$_v$—, wherein one of the CH$_2$ moieties is optionally replaced with —C(=O)—, —NH— or —NHC(=O)—, is illustrated by, but not limited to, the following:

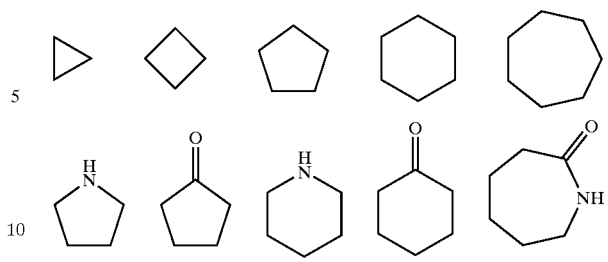

The moiety formed when, in the definition of $R^6$ and $R^7$, $R^6$ and $R^7$ are joined to form a ring, is illustrated by, but not limited to, the following:

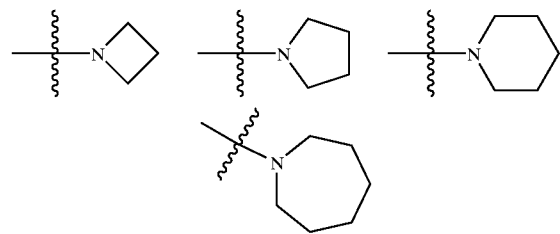

Lines drawn into the ring systems from substituents (such as from $R^8$, $R^9$ etc.) indicate that the indicated bond may be attached to any of the substitutable ring carbon and nitrogen atoms.

Preferably, $R^{1a}$ and $R^{1b}$ are independently selected from: hydrogen, —N(R$^{10}$)$_2$, R$^{10}$C(O)NR$^{10}$— or unsubstituted or substituted $C_1$–$C_6$ alkyl wherein the substituent on the substituted $C_1$–$C_6$ alkyl is selected from unsubstituted or substituted phenyl, —N(R$^{10}$)$_2$, R$^{10}$O— and R$^{10}$C(O)NR$^{10}$—. More preferably, $R^{1a}$ and $R^{1b}$ are hydrogen.

Preferably, $R^{1c}$ is independently selected from: hydrogen, or unsubstituted or substituted $C_1$–$C_6$ alkyl wherein the substituent on the substituted $C_1$–$C_6$ alkyl is selected from unsubstituted or substituted phenyl, —N(R$^{10}$)$_2$, R$^{10}$O— and R$^{10}$C(O)NR$^{10}$—.

Preferably, $R^{1e}$ is selected from:
a) hydrogen,
b) substituted or unsubstituted aryl, substituted or unsubstituted heterocycle, $C_3$–$C_6$ cycloalkyl, $C_2$–$C_6$ alkenyl, $C_2$–$C_6$ alkynyl, R$^{10}$O—, —N(R$^{10}$)$_2$, R$^{10}$C(O)NR$^{10}$—, (R$^{10}$)$_2$N—C(O)—, or R$^{10}$OC(O)—, and
c) unsubstituted or substituted $C_1$–$C_6$ alkyl wherein the substituent on the substituted $C_1$–$C_6$ alkyl is selected from substituted or unsubstituted aryl, substituted or unsubstituted heterocycle, halo, perfluoroalkyl, $C_3$–$C_6$ cycloalkyl, $C_2$–$C_6$ alkenyl, $C_2$–$C_6$ alkynyl, R$^{10}$O—, R$^4$S(O)$_m$—, R$^{10}$C(O)NR$^{10}$—, (R$^{10}$)$_2$N—C(O)—, CN, (R$^{10}$)$_2$N—C(NR$^{10}$)—, R$^4$S(O)$_2$NR$^{10}$—, —S(O)$_2$N(R$^{10}$)$_2$, R$^{10}$C(O)—, R$^{10}$OC(O)—, —N(R$^{10}$)$_2$, and R$^{11}$OC(O)—NR$^{10}$—;
or two $R^{1e}$s on the same carbon atom may be combined to form —(CH$_2$)$_v$—, wherein one of the CH$_2$ moieties is optionally replaced with —C(=O)—, —NH— or —NHC(=O)—.

Preferably, $R^{1d}$ is selected from:
a substituted or unsubstituted aryl, substituted or unsubstituted heterocycle, $C_3$–$C_6$ cycloalkyl, $C_2$–$C_6$ alkenyl, $C_2$–$C_6$ alkynyl, R$^{10}$O—, —N(R$^{10}$)$_2$, R$^{10}$C(O)NR$^{10}$—, (R$^{10}$)$_2$N—C(O)—, or R$^{10}$OC(O)—, and
b unsubstituted or substituted $C_1$–$C_6$ alkyl, unsubstituted or substituted $C_2$–$C_6$ alkenyl or unsubstituted or substituted $C_2$-$C_6$ alkynyl, wherein the substituent on the substituted $C_1$-$C_6$ alkyl, substituted $C_2$-$C_6$ alkenyl or substituted $C_2$-$C_6$ alkynyl is selected from substituted or unsubstituted aryl, substituted or unsubstituted heterocycle, halo, $C_1$-$C_6$ perfluoroalkyl, $C_3$-$C_6$ cycloalkyl, $C_2$-$C_6$ alkenyl, $C_2$-$C_6$ alkynyl, $R^{10}O$—, $R^4S(O)_m$—, $R^{10}C(O)NR^{10}$—, $(R^{10})_2N$—$C(O)$—, CN, $(R^{10})_2N$—$C(NR^{10})$—, $R^4S(O)_2NR^{10}$—, —$S(O)_2N(R^{10})_2$, $R^1C(O)$—, $R^{10}OC(O)$—, —$N(R^{10})_2$, and $R^{11}OC(O)$—$NR^{10}$—.

Preferably, $R^4$ is $C_1$-$C_6$ alkyl.

Preferably, $R^6$ and $R^7$ is selected from: hydrogen, unsubstituted or substituted $C_1$-$C_6$ alkyl, unsubstituted or substituted aryl and unsubstituted or substituted cycloalkyl.

Preferably, $R^9$ and $R^{9a}$ are hydrogen or methyl.

Preferably, $R^{10}$ is selected from H, $C_1$-$C_6$ alkyl and benzyl.

Preferably, $A^1$ and $A^2$ are independently selected from a bond, —$C(O)NR^{10}$—, —$NR^{10}C(O)$—, O, —$N(R^{10})$—, —$NR^{10}C(O)NR^{10}$—, —$S(O)_2N(R^{10})$— and —$N(R^{10})S(O)_2$—. More preferably, $A^1$ is selected from a bond and O. More preferably, $A^2$ is a bond.

Preferably, V is selected from heteroaryl and aryl. More preferably, V is phenyl or pyridyl.

Preferably, X is selected from —$NR^{10}C(O)$—, O, —$N(R^{10})$— and —$N(R^{10})S(O)_2$—.

Preferably, $Z^1$ is selected from unsubstituted or substituted aryl and unsubstituted or substituted heteroaryl. More preferably, $Z^1$ is selected from unsubstituted or substituted phenyl, unsubstituted or substituted naphthyl, unsubstituted or substituted pyridyl, unsubstituted or substituted furanyl and unsubstituted or substituted thienyl. Still more preferably, $Z^1$ is selected from unsubstituted or substituted phenyl and unsubstituted or substituted naphthyl.

Preferably, $Z^2$ is selected from a bond, unsubstituted or substituted aryl and unsubstituted or substituted heteroaryl. More preferably, $Z^2$ is selected from a bond, unsubstituted or substituted phenyl, unsubstituted or substituted naphthyl, unsubstituted or substituted pyridyl, unsubstituted or substituted furanyl and unsubstituted or substituted thienyl. Still more preferably, $Z^2$ is selected from a bond and unsubstituted or substituted phenyl.

Preferably, W is selected from imidazolyl, pyridinyl and triazolyl. More preferably, W is selected from imidazolyl and pyridyl.

Preferably, n is 0, 1, or 2.
Preferably, r is 1 or 2.
Preferably p is 0, 1 or 2.
Preferably s is 0 or 1.
Preferably, the moiety

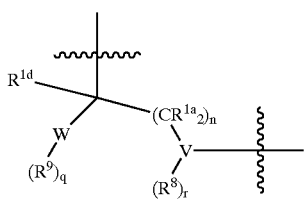

is selected from:

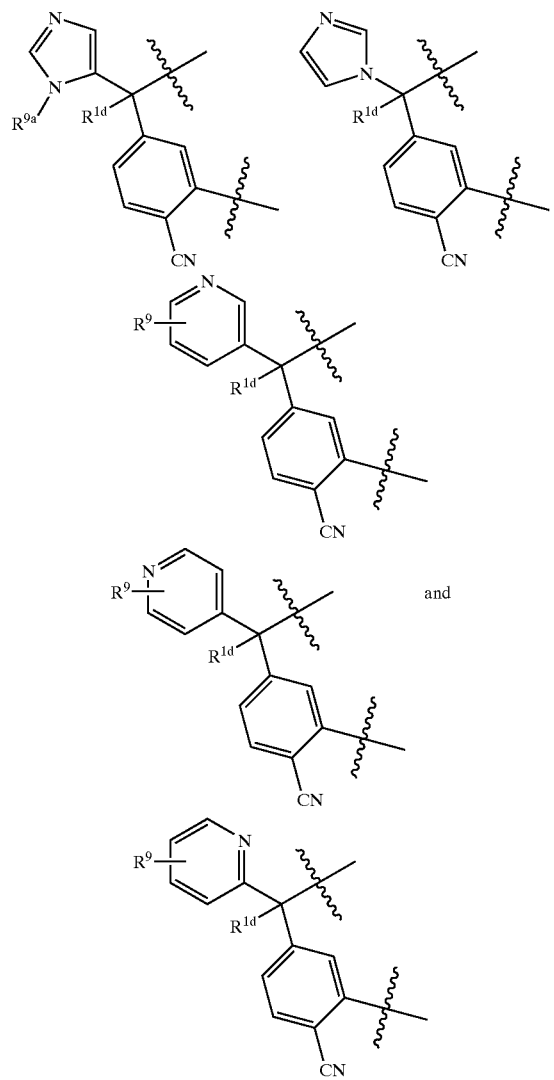

and wherein $R^{9a}$ is selected from hydrogen and methyl.

It is intended that the definition of any substituent or variable (e.g., $R^{1a}$, $R^9$, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–13, in addition to other standard manipulations such as ester hydrolysis, cleavage of protecting groups, etc., as may be known in the literature or exemplified in the experimental procedures. Substituents $R^{sub}$ and $R^{sub'}$, as shown in the Schemes, represent the substituents on $Z^1$ and $Z^2$ and other moieties of the instant compounds; however their point of attachment to the ring is illustrative only and is not meant to be limiting. It is understood that one of ordinary skill in the art would be readily able to substitute commercially available or readily prepared suitably substituted aromatic moieties for those unsubstituted moieties illustrated in the schemes.

These reactions may be employed in a linear sequence to provide the compounds of the invention or they may be used to synthesize fragments which are subsequently joined by the alkylation reactions described in the Schemes.

Synopsis of Schemes 1–13:

The requisite intermediates are in some cases commercially available, or can be prepared according to literature procedures. In Scheme 1, for example, the synthesis of a key intermediate in the preparation of macrocyclic compounds of the instant invention and its incorporation into the macrocycle is generally outlined. A suitably substituted halohydroxytoluene I is oxidized and reacted with a suitably substituted nucleophilic heteroaryl moiety to form the intermediate III. Intermediate III is oxidized to key intermediate IV, which may be alkylated to key hydroxy intermediate V. Intermediate V may be utilized in the synthesis of the macrocyclic compound or the hydroxyl may be further elaborated to the corresponding amine VI as shown. The Scheme illustrates the formation of a macrocyclic compound wherein "X" is an amide moiety. Coupling of amine VI to a phenolic alkanoic acid, followed by deprotection of the phenol and cesium carbonate mediated coupling provides the instant compound VII. This last cyclization reaction depends on the presence of an electron withdrawing moiety (such as nitro, cyano, and the like) either ortho or para to the halogen atom.

Scheme 2 illustrates the synthesis of a compound of the instant invention wherein W is the preferred imidazolyl moiety. Thus, the trityl protected halo imidazolyl is reacted with the aldehyde II to provide the alcohol VIII. The imidazolyl may be alkylated on the nitrogen, in a series of steps, and then the hydroxy moiety is oxidized to the ketone IX. The ketone IX may be further functionalized to intermediates X and XI, as illustrated in Scheme I and elaborated to the instant compound XII.

Scheme 3 illustrated the preparation of the instant compound wherein "X" is an ester moiety as in compound XIII.

The alkanoic acid utilized in Scheme 1 may be converted to the aldehyde XIV, as shown in Scheme 4, which may then be utilized to reductively alkylate key intermediate XI. The resulting amine may be alkylated as shown, then may undergo the previously described steps to provide the instant compound XV.

If allyl Grignard is reacted with intermediate IX, the resulting allyl compound may be oxidized to provide the key intermediate aldehyde XVI, as shown in Scheme 5. Protection of the hydroxyl moiety provides intermediate XVII, which may then be used to reductively alkylate a variety of suitably substituted amines, such as the commercially available aminobenzylthiophenol shown. The previously illustrated steps then lead to the instant compound XVIII.

As shown in Scheme 6, intermediate IX may alternatively be converted to the protected imine XIX, which may also react with allyl Grignard to provide, after oxidation intermediate XX. Intermediate XX may then be reacted with an amine to eventually provide the instant compound XXI.

The benzyl protected intermediate XVIIa may be alternatively oxidized to the carboxylic acid XXII, which may be converted to the acid chloride XXIII, as illustrated in Scheme 7. This acid chloride may be reacted with a suitably substituted aminomethylphenol, such as the mesyl protected compound XXIV, to provide intermediate XXV. The previously illustrated cyclization conditions deprotect the phenol moiety and cyclize to provide, after further oxygen deprotection instant compound XXVI, which may be reduced to provide instant compound XXVII.

Incorporation of a sulfur containing moiety for $A^1$ in the instant compounds is illustrated in Scheme 8. Thus the acid chloride XXIII is reacted with the disulfide protected aniline XXVIII to provide the intermediate XXIX. The sulfide moiety is liberated with dithiothrietol to provide the mercaptan, which undergoes cyclization under cesium carbonate conditions to provide the instant compound XXX. The sulfur may be oxidized to either the sulfone or sulfoxide XXXI.

Scheme 9 illustrates incorporation of a naphthyl moiety for "$Z^1$".

Incorporation of a nitrogen-containing moiety for "$A^1$" is illustrated in Scheme 10. Thus, the aldehyde of intermediate XVII may be converted to the homologous amine in intermediate XXXII. Intermediate XXXII may be reacted with a suitably substituted acid chloride XXXIII to provide compound XXXIV, which can be deprotected and cyclized in the presence of potassium t-butoxide to provide the instant compound XXXV.

Scheme 11 illustrates the synthesis of the instant compound XXXVI wherein "X" is a sulfonamide moiety.

Scheme 12 illustrates the synthetic strategy that is employed when the $R^8$ substituent is not an electronic withdrawing moiety either ortho or para to the fluorine atom. In the absence of the electron withdrawing moiety, the intramolecular cyclization can be accomplished via an Ullmann reaction. Thus, a suitably substituted iodo benzaldehyde XXXVII may be employed in place of intermediate II. Incorporation of a "W" moiety, in this instance a pyridyl group, followed by the previously described elaboration provides the intermediate XXXVIII. Intramolecular cyclization may then be affected under Ullmann conditions to provide the instant compound IXL.

Use of intermediate XI to provide an instant compound having a sulfonamide moiety for "X" is illustrated in Scheme 13.

SCHEME 1
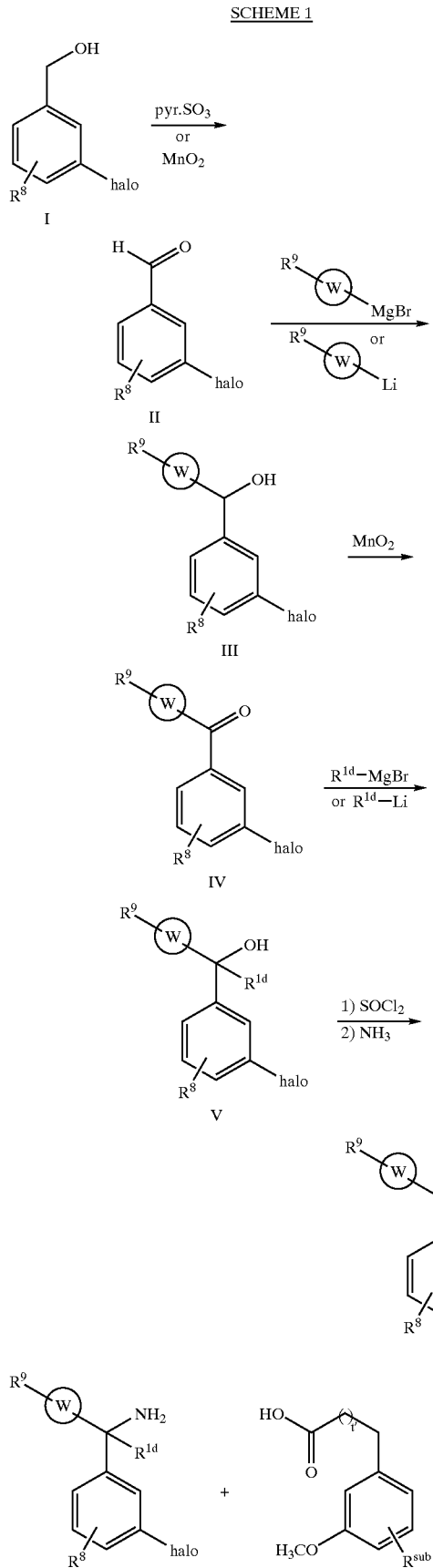
SCHEME 2
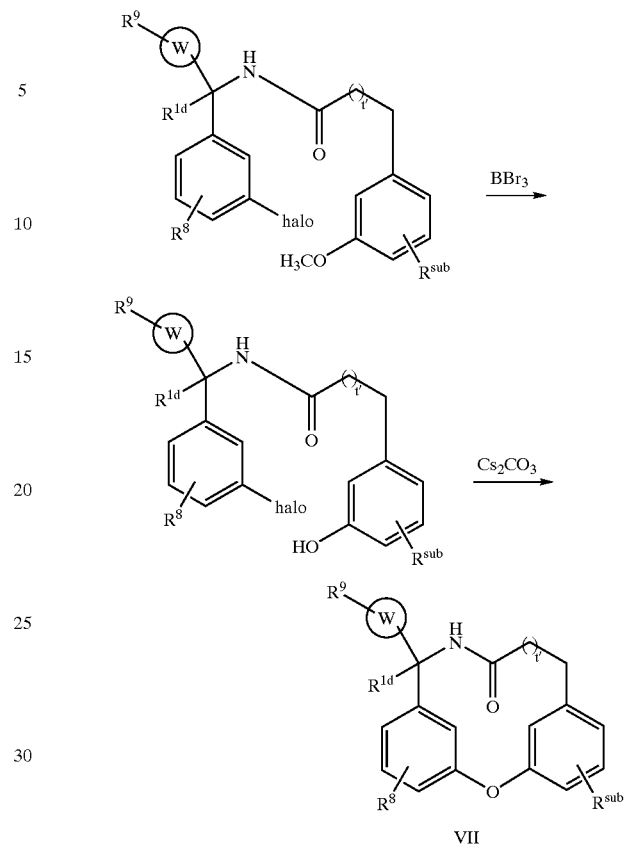
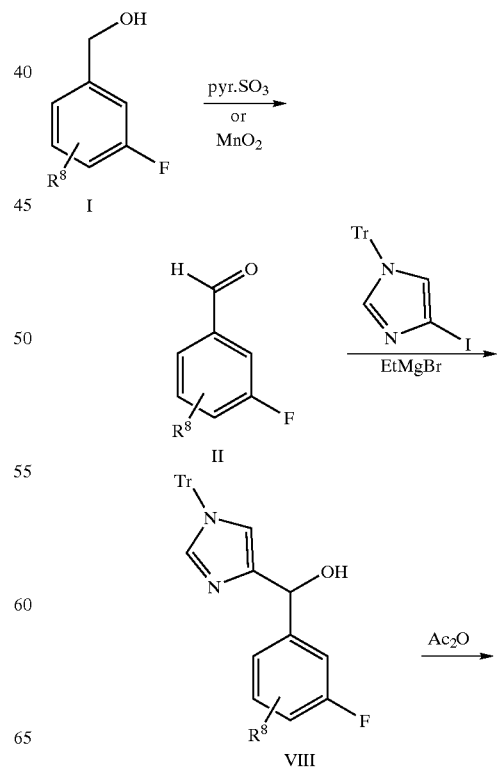

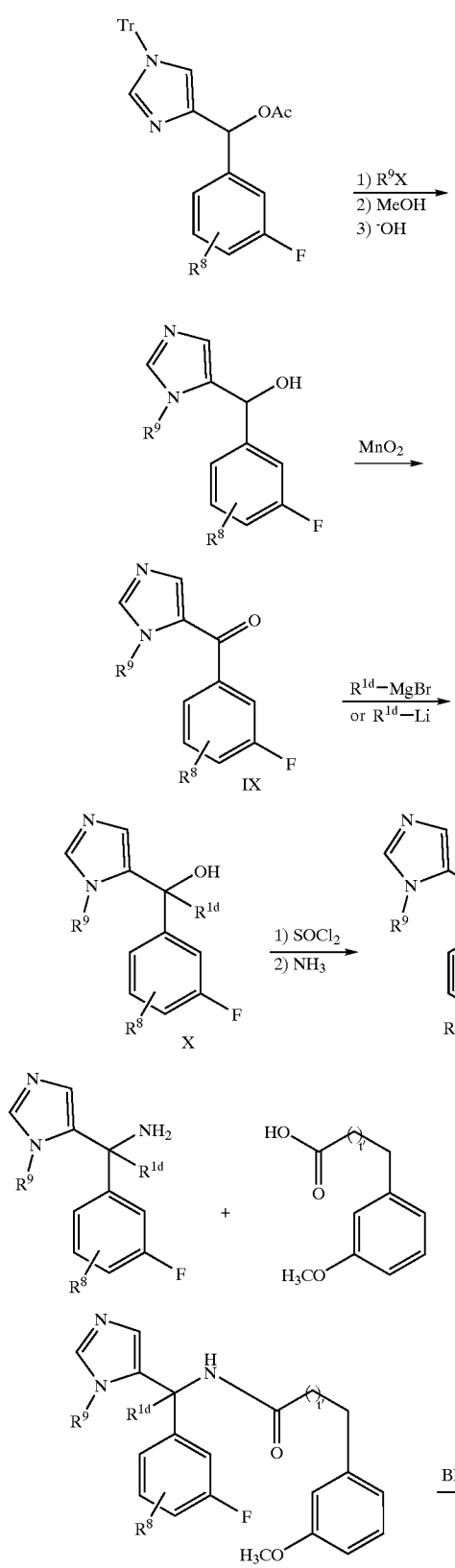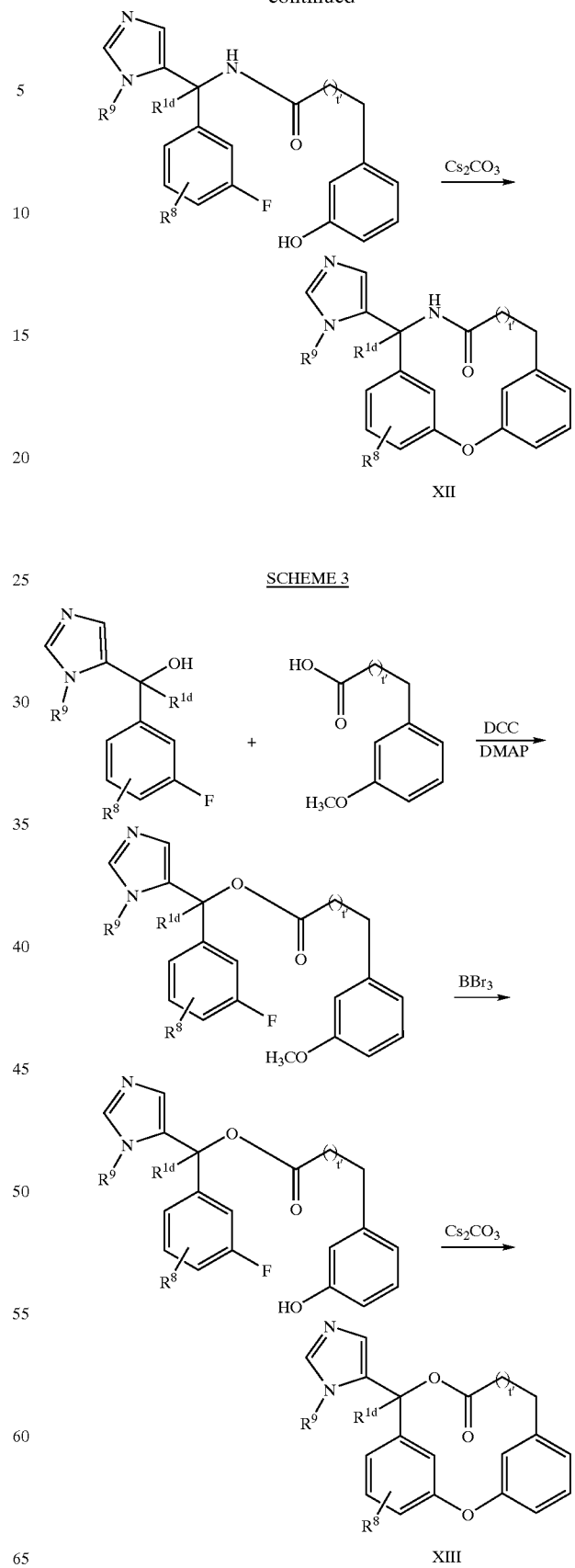

SCHEME 4
SCHEME 5
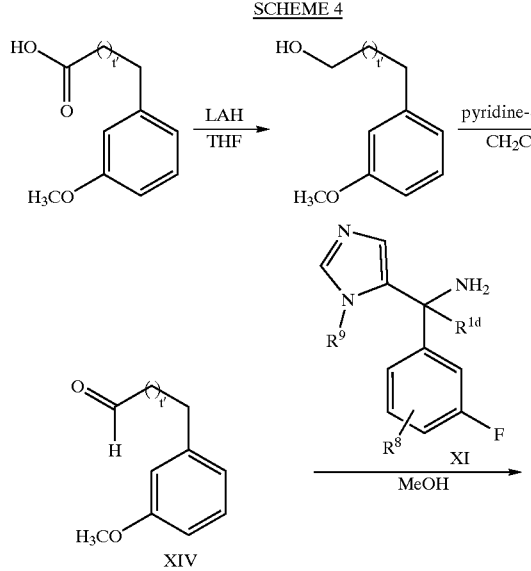
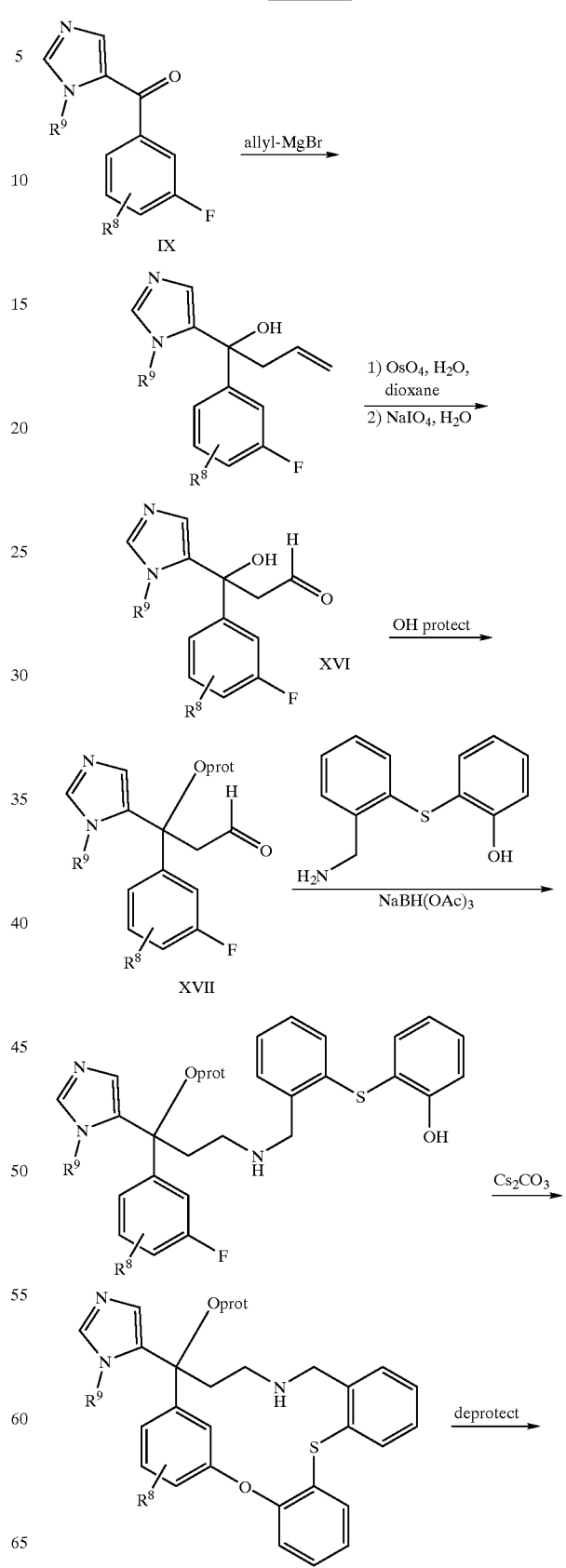

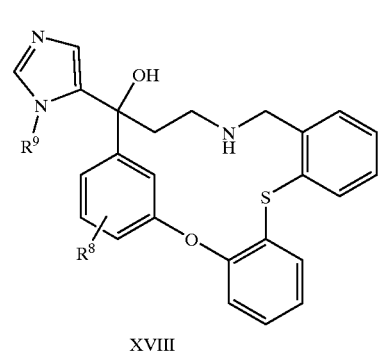
XVIII
SCHEME 6
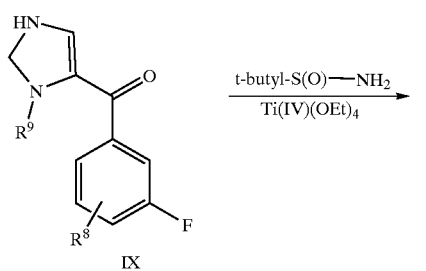
IX
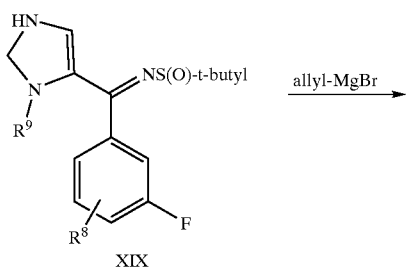
XIX
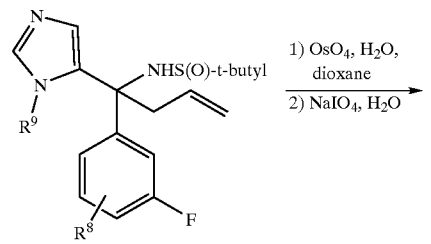
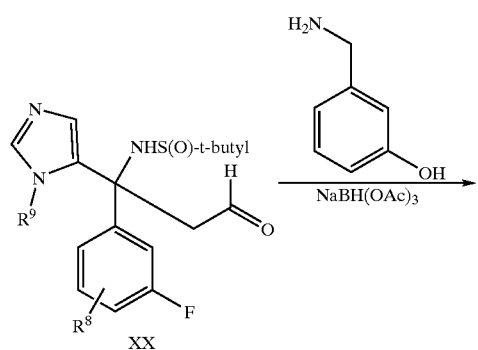
XX
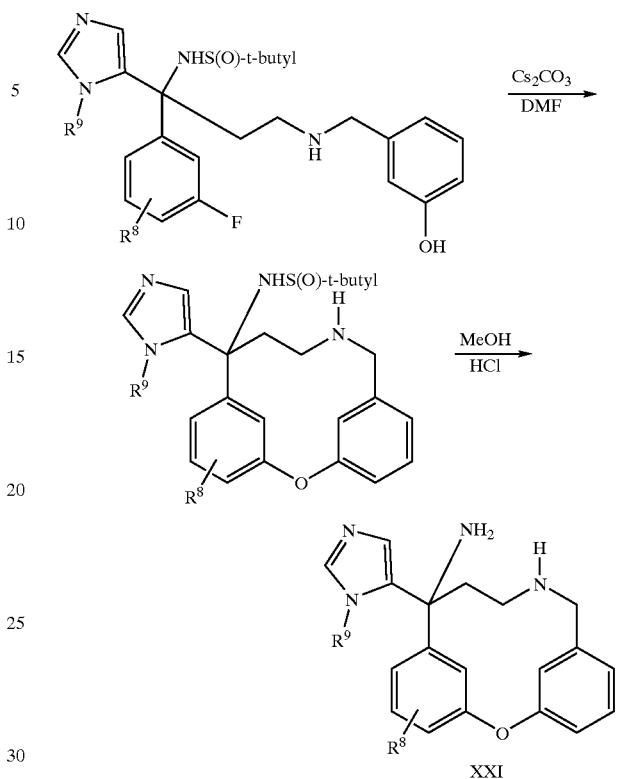
XXI
SCHEME 7
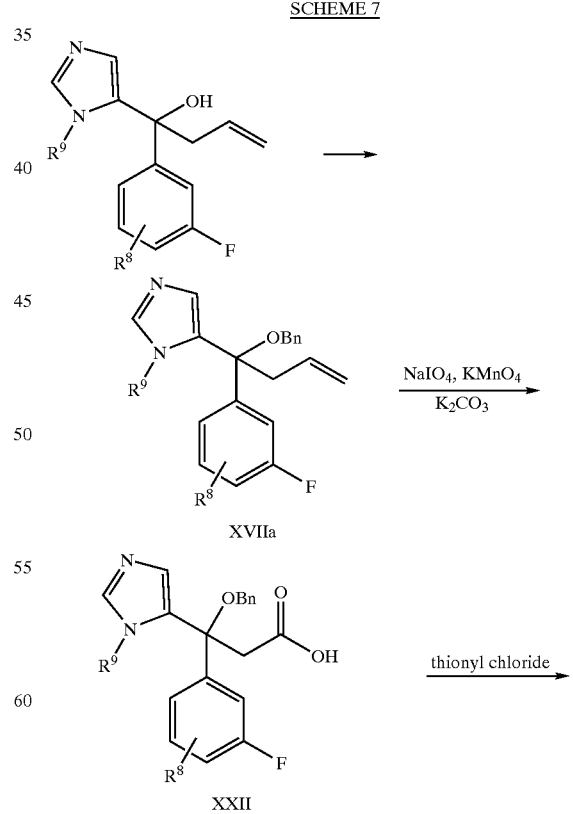
XXII

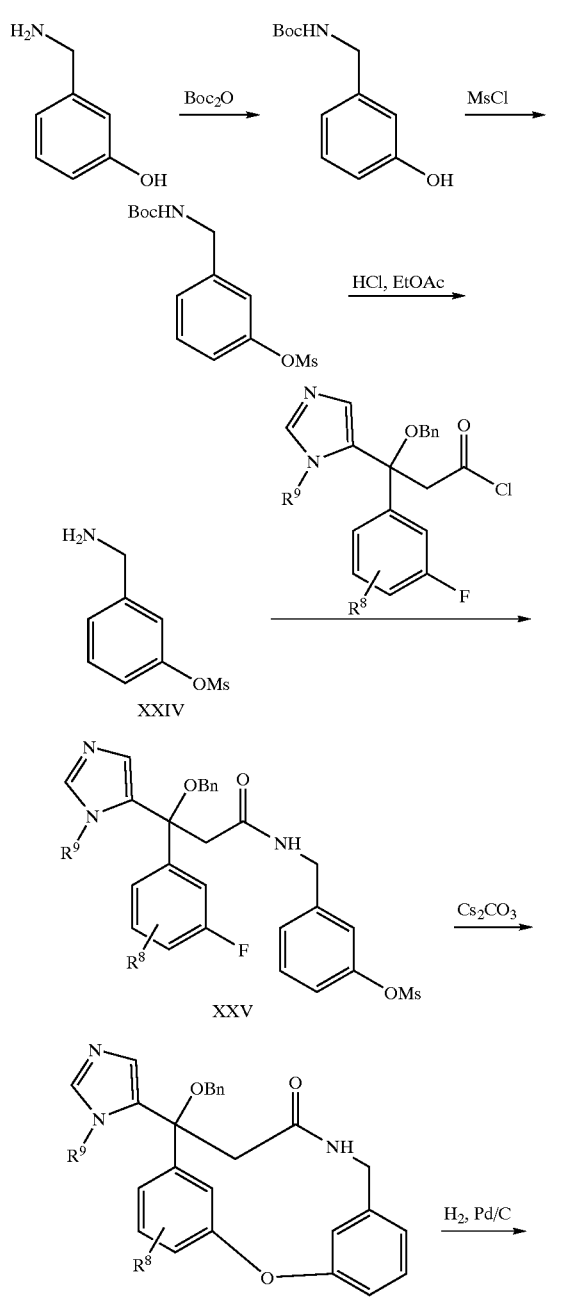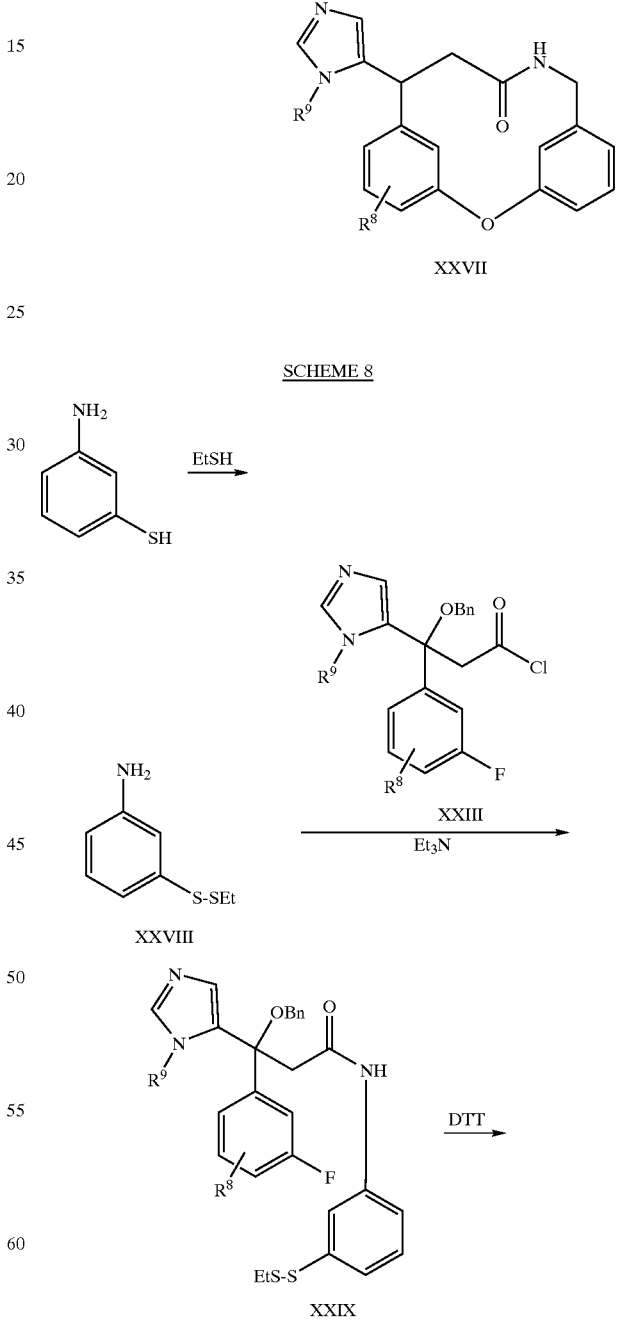
SCHEME 8

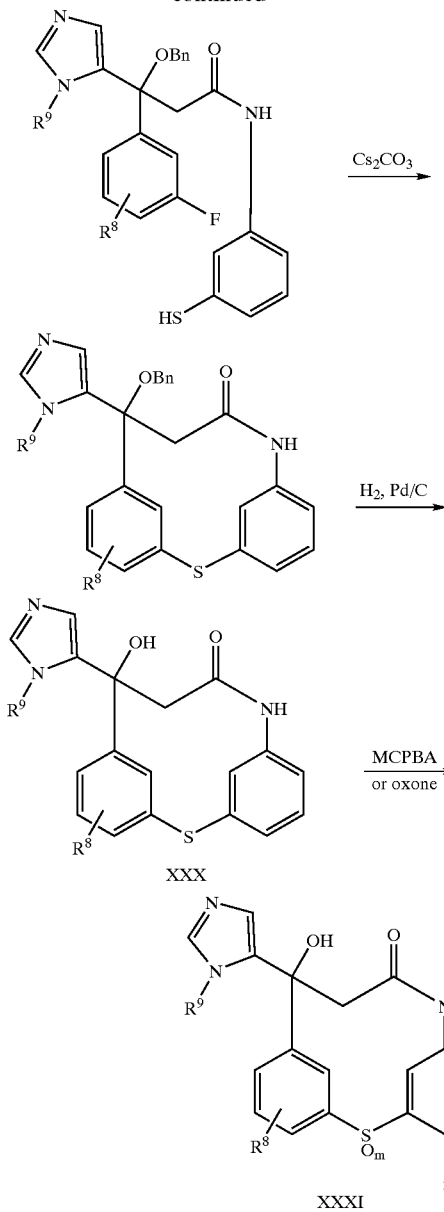
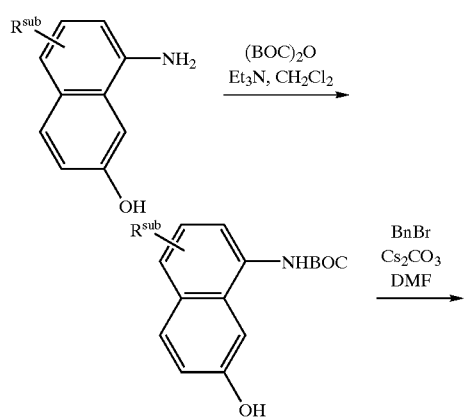
SCHEME 9
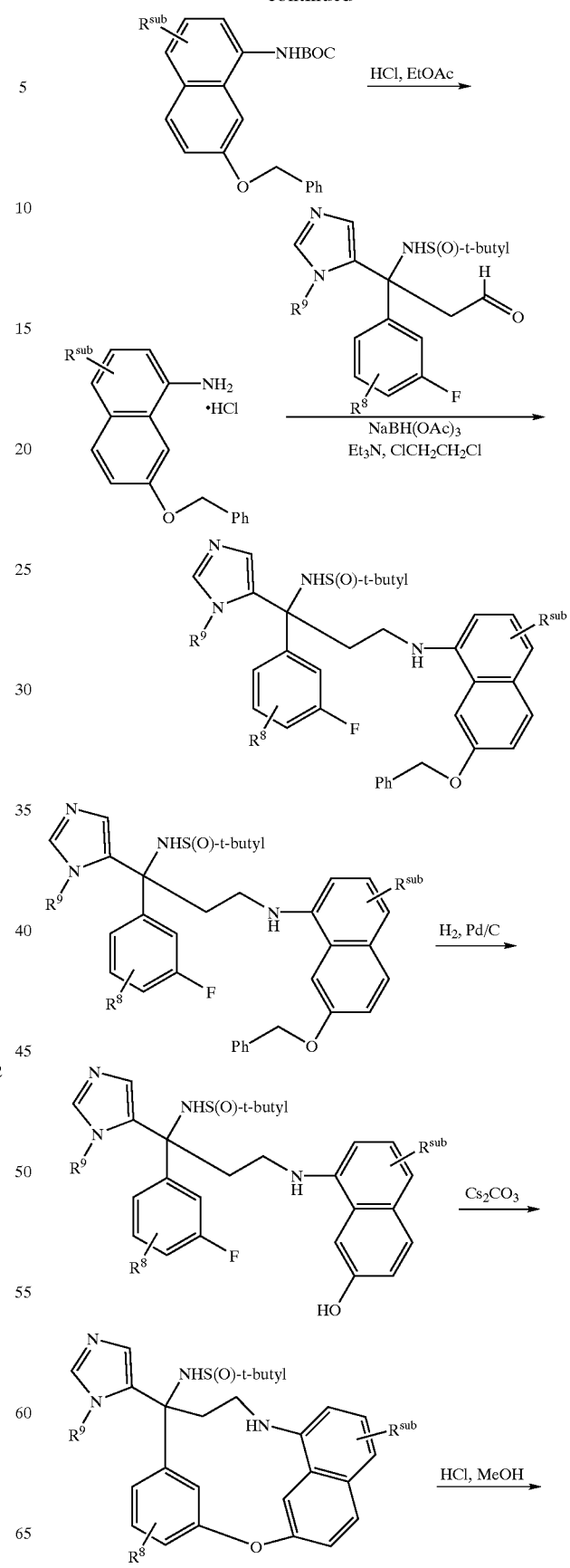

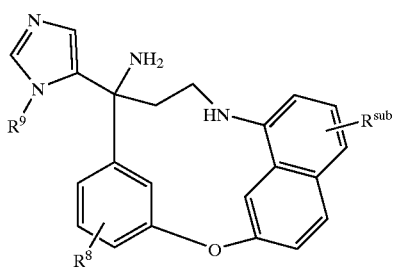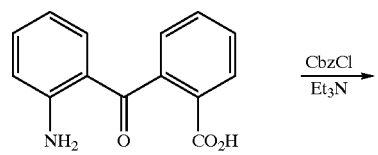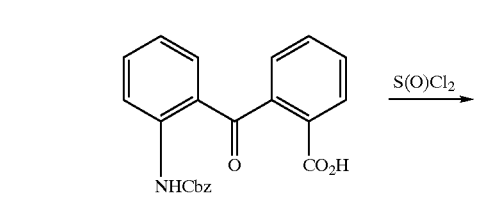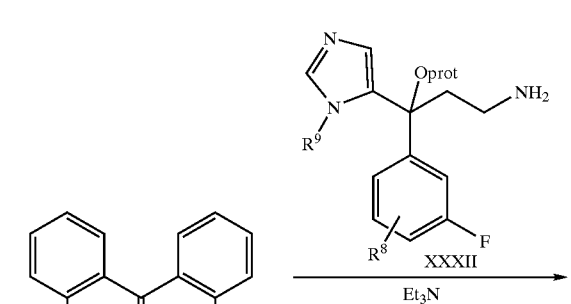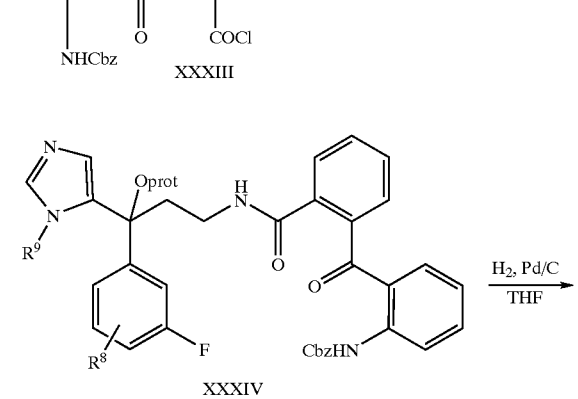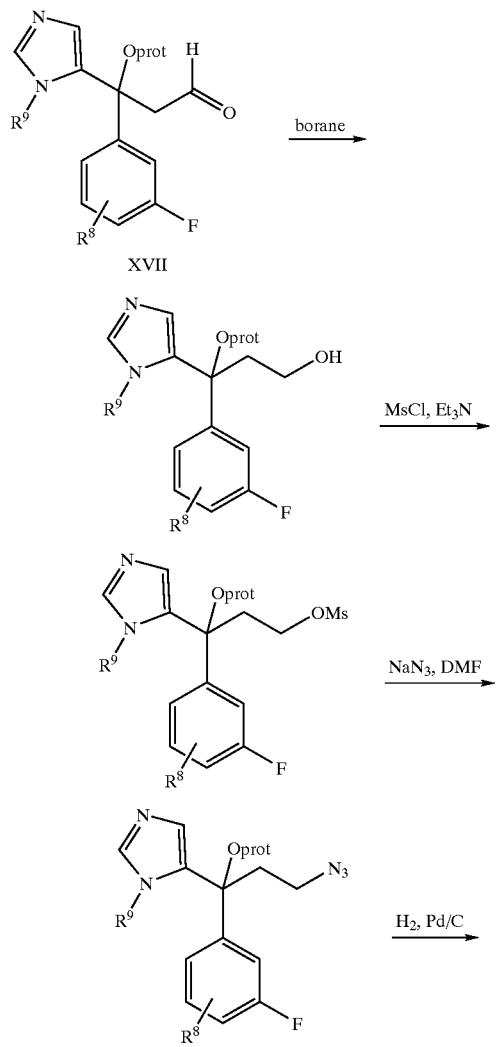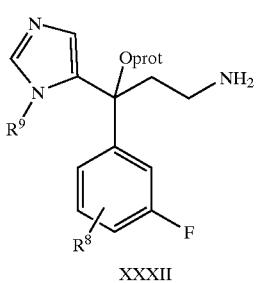
SCHEME 10

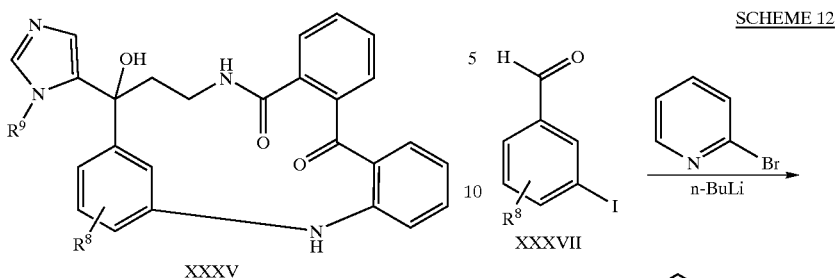
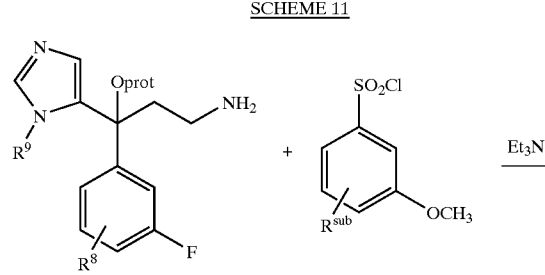
SCHEME 11
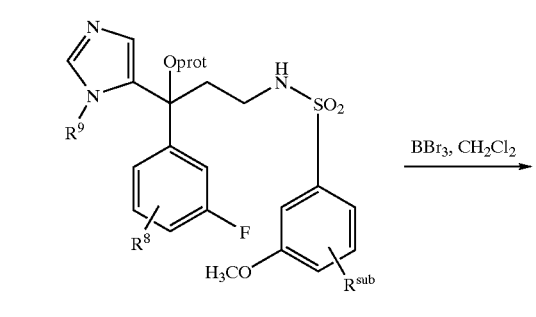
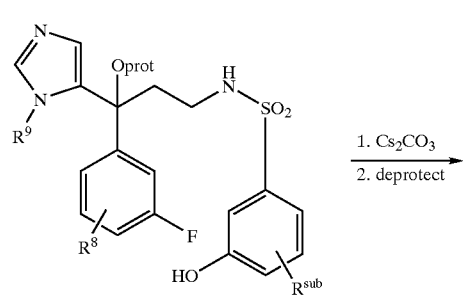
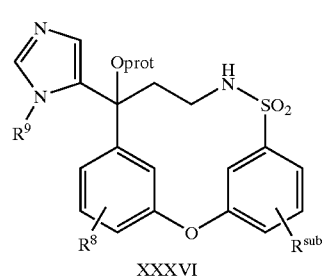
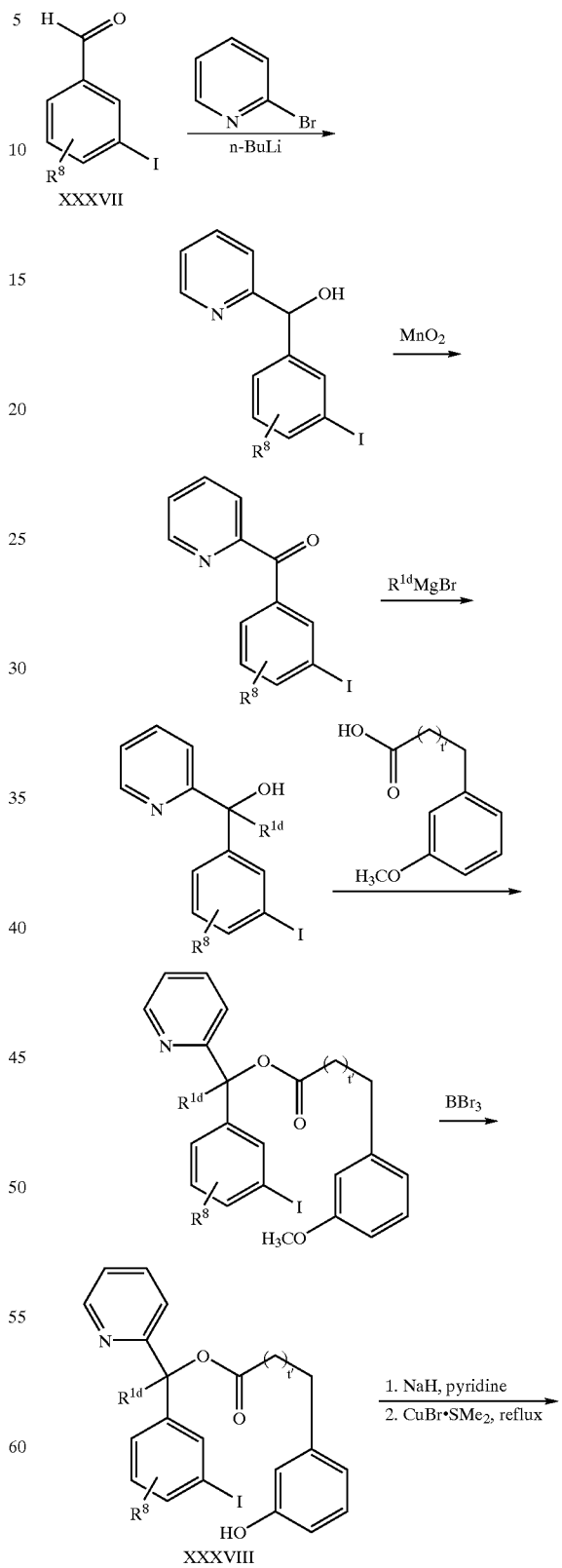

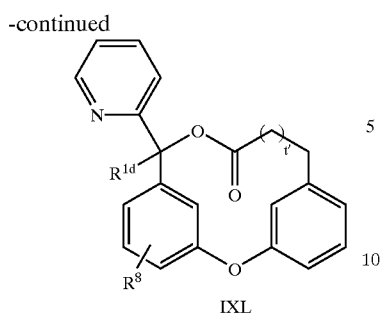

IXL

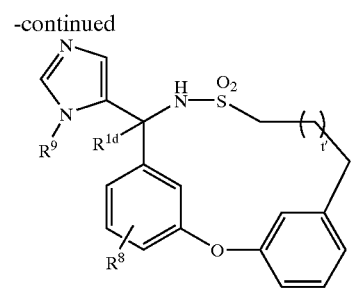

SCHEME 13

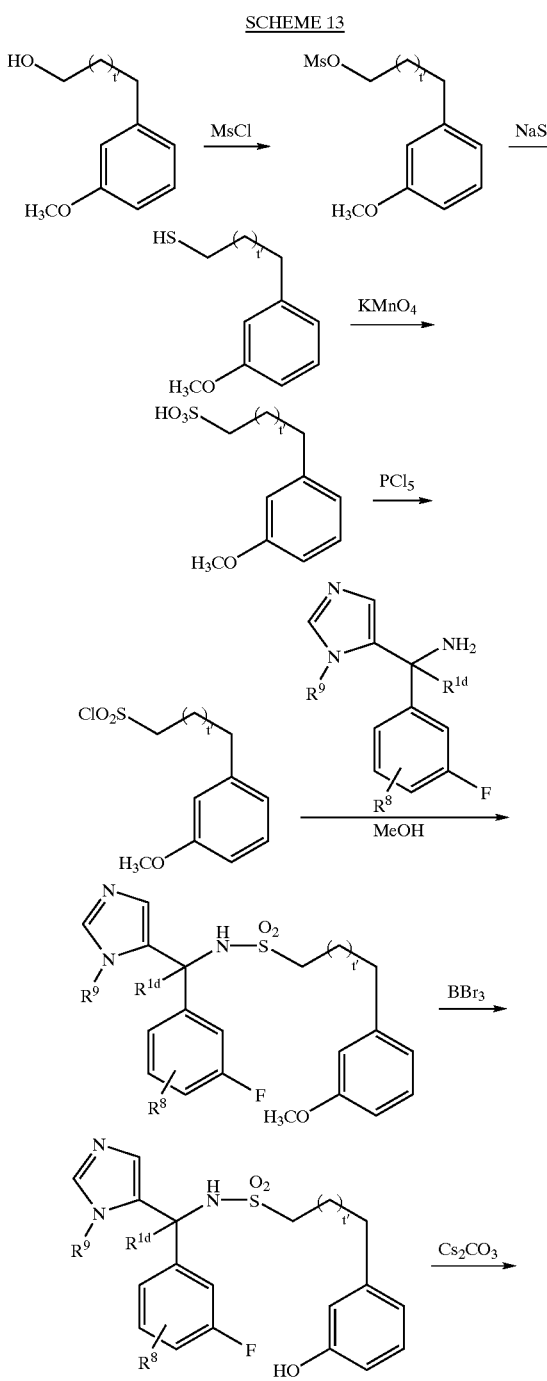

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 8, is at least 100 times greater than the in vitro activity of the same compound against geranylgeranyl-protein transferase-type I in the assay described in Example 9. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein.

When measuring such $IC_{50}$s and $EC_{50}$s the assays described in Example 13 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 12 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Examples 12, it is preferred that the dual inhibitor compound has an in vitro inhibitory activity ($IC_{50}$) that is less than about 12 µM against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 12.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the composition is useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of the instant invention may also be useful in the prevention and treatment of endometriosis, uterine fibroids, dysfunctional uterine bleeding and endometrial hyperplasia.

In such methods of prevention and treatment as described herein, the prenyl-protein transferase inhibitors of the instant invention may also be co-administered with other well known therapeutic agents that are selected for their particular usefulness against the condition that is being treated. For example, the prenyl-protein transferase inhibitor may be useful in farther combination with drugs known to supress the activity of the ovaries and slow the growth of the endometrial tissue. Such drugs include but are not limited to oral contraceptives, progestins, danazol and GnRH (gonadotropin-releasing hormone) agonists.

Administration of the prenyl-protein transferase inhibitor may also be combined with surgical treatment of endometriosis (such as surgical removal of misplaced endometrial tissue) where appropriate.

The instant compounds may also be useful as inhibitors of corneal inflammation. These compounds may improve the treatment of corneal opacity which results from cauterization-induced corneal inflammation. The instant compounds may also be useful in reducing corneal edema and neovascularization. (K. Sonoda et al., *Invest. Ophthalmol. Vis. Sci.*, 1998, vol. 39, p 2245–2251).

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

Additionally, the compounds of the instant invention may be administered to a mammal in need thereof using a gel extrusion mechanism (GEM) device, such as that described in U.S. Ser. No. 60/144,643, filed on Jul. 20, 1999, which is hereby incorporated by reference.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUSTM model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.) The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of prenyl-protein transferase may be used in conjunction with other methods of treating cancer and/or tumors, including radiation therapy and surgery. It is further understood that any of the therapeutic agents described herein may also be used in combination with a compound of the instant invention and an antineoplastic agent.

Examples of an antineoplastic agent include, in general, microtubule-stabilizing agents such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, for example, nitrogen mustards, ethyleneimine compounds, alkyl sulfonates and other compounds with an alkylating action such as nitrosoureas, cisplatin, and dacarbazine; anti-metabolites, for example, folic acid, purine or pyrimidine antagonists; epidophyllotoxin; an antineoplastic enzyme; a topoisomerase inhibitor; procarbazine; mitoxantrone; platinum coordination complexes; biological response modifiers and growth inhibitors; mitotic inhibitors, for example, vinca alkaloids and derivatives of podophyllotoxin; cytotoxic antibiotics; hormonal/anti-hormonal therapeutic agents, haematopoietic growth factors and antibodies (such as trastuzumab, also known as Herceptin™).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, dactinomycin, mechlorethamine (nitrogen mustard), streptozocin, cyclophosphamide, carmustine (BCNU), lomustine (CCNU), procarbazine, mitomycin, cytarabine, etoposide, methotrexate, bleomycin, chlorambucil, camptothecin, CPT-11, topotecan, ara-C, bicalutamide, flutamide, leuprolide, pyridobenzoindole derivatives, interferons and interleukins. Particular examples of antineoplastic, or chemotherapeutic, agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. See also, R. J. Gralla, et al., Cancer Treatment Reports, 68(1), 163–172 (1984).

The preferred class of antineoplastic agents is the taxanes and the preferred antineoplastic agent is paclitaxel.

The compounds of the instant invention may also be co-administered with antisense oligonucleotides which are specifically hybridizable with RNA or DNA deriving from human ras gene. Such antisense oligonucleotides are described in U.S. Pat. No. 5,576,208 and PCT Publ. No. WO 99/22772. The instant compounds are particularly useful when co-administered with the antisense oligonucleotide comprising the amino acid sequence of SEQ.ID.NO: 2 of U.S. Pat. No. 5,576,208.

Certain compounds of the instant invention may exhibit very low plasma concentrations and significant interindividual variation in the plasma levels of the compound. It is believed that very low plasma concentrations and high intersubject variability achieved following administration of certain prenyl-protein transferase inhibitors to mammals may be due to extensive metabolism by cytochrome P450 enzymes prior to entry of drug into the systemic circulation. Prenyl-protein transferase inhibitors may be metabolized by cytochrome P450 enzyme systems, such as CYP3A4, CYP2D6, CYP2C9, CYP2C19 or other cytochrome P450 isoform. If a compound of the instant invention demonstrates an affinity for one or more of the cytochrome P450 enzyme systems, another compound with a higher affinity for the P450 enzyme(s) involved in metabolism should be administered concomitantly. Examples of compounds that have a comparatively very high affinity for CYP3A4, CYP2D6, CYP2C9, CYP2C19 or other P450 isoform include, but are not limited to, piperonyl butoxide, troleandomycin, erythromycin, proadifen, isoniazid, allylisopropylacetamide, ethinylestradiol, chloramphenicol, 2-ethynylnaphthalene and the like. Such a high affinity compound, when employed in combination with a compound of formula A, may reduce the inter-individual variation and increase the plasma concentration of a compound of formula A to a level having substantial therapeutic activity by inhibiting the metabolism of the compound of formula A. Additionally, inhibiting the metabolism of a compound of the instant invention prolongs the pharmacokinetic half-life, and thus the pharmacodynamic effect, of the compound.

A compound of the present invention may be employed in conjunction with antiemetic agents to treat nausea or emesis, including acute, delayed, late-phase, and anticipatory emesis, which may result from the use of a compound of the present invention, alone or with radiation therapy. For the prevention or treatment of emesis a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, or a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712. For the treatment or prevention of emesis, conjunctive therapy with a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913,0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

A particularly preferred neurokinin-1 receptor antagonist for use in conjunction with the compounds of the present invention is 2-(R)-(1-(R)-(3,5-bis (trifluoromethyl)phenyl) ethoxy)-3-(S)-(4-fluorophenyl)-4-(3-(5-oxo-1H,4H-1,2,4-triazolo) methyl)morpholine, or a pharmaceutically acceptable salt thereof, which is described in U.S. Pat. No. 5,719,147.

For the treatment of cancer, it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). hi general, the currently available dosage forms of the known therapeutic agents for use in such combinations will be suitable.

For example, a compound of the present invention may be presented together with another therapeutic agent in a combined preparation, such as with an antiemetic agent for simultaneous, separate, or sequential use in the relief of emesis associated with employing a compound of the present invention and radiation therapy. Such combined preparations may be, for example, in the form of a twin pack. A preferred combination comprises a compound of the present invention with antiemetic agents, as described above.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435, 047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, and WO 98/44797, published on Oct. 15, 1998, which are incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5 integrin, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

The instant compounds may also be useful in combination with an inhibitor of 3-hydroxy-3-methylglutaryl-CoA reductase (HMG-COA reductase) for the treatment of cancer. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. No. 4,231,938; 4,294,926; 4,319,039), simvastatin (ZOCOR®; see U.S. Pat. No. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

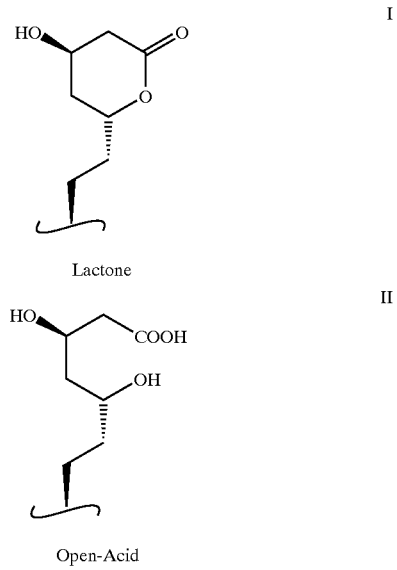

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, omithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described above and the other pharmaceutically active agent(s) within its approved dosage range. Combinations of the instant invention may alternatively be used sequentially with known pharmaceutically acceptable agent(s) when a multiple combination formulation is inappropriate.

The instant compounds may also be useful in combination with prodrugs of antineoplastic agents. In particular, the instant compounds may be co-administered either concurrently or sequentially with a conjugate (termed a "PSA conjugate") which comprises an oligopeptide, that is selectively cleaved by enzymatically active prostate specific antigen (PSA), and an antineoplastic agent. Such co-administration will be particularly useful in the treatment of prostate cancer or other cancers which are characterized by the presence of enzymatically active PSA in the immediate surrounding cancer cells, which is secreted by the cancer cells.

Compounds which are PSA conjugates and are therefore useful in such a co-administration, and methods of synthesis thereof, can be found in the following patents, pending patent applications and publications which are herein incorporated by reference:
U.S. Pat. No. 5,599,686, granted on Feb. 4, 1997;
WO 96/00503 (Jan. 11, 1996); U.S. Ser. No. 08/404,833, filed on Mar. 15, 1995;
U.S. Ser. No. 08/468,161, filed on Jun. 6, 1995;
U.S. Pat. No. 5,866,679, granted on Feb. 2, 1999;
WO 98/10651 (Mar. 19, 1998); U.S. Ser. No. 08/926,412, filed on Sep. 9, 1997;
WO 98/18493 (May 7, 1998); U.S. Ser. No. 08/950,805, filed on Oct. 14, 1997;
WO 99/02175 (Jan. 21, 1999); U.S. Ser. No. 09/112,656, filed on Jul. 9, 1998; and
WO 99/28345 (Jun. 10, 1999); U.S. Ser. No. 09/193,365, filed on Nov. 17, 1998.

Compounds which are described as prodrugs wherein the active therapeutic agent is released by the action of enzymatically active PSA and therefore may be useful in such a co-administration, and methods of synthesis thereof, can be found in the following patents, pending patent applications and publications, which are herein incorporated by reference: WO 98/52966 (Nov. 26, 1998).

All patents, publications and pending patent applications identified are herein incorporated by reference.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

EXAMPLES

Examples provided are intended to assist in a further understanding of the invention. Particular materials employed, species and conditions are intended to be further illustrative of the invention and not limitative of the reasonable scope thereof.

Example 1

Preparation of 5-(4-Cyano-8-methyl-10-oxo-2-oxa-9-aza-tricyclo[11.3.1.1$^{3,7}$]octadeca -1(16),3(18),4,6, 13(17),14-hexaen-8-yl)-1-methyl-1H-imidazol-1-ium; 2,2,2-trifluoroacetate Step A: Preparation of 4-Bromo-3-fluorobenzoic Acid 4-Bromo-3-fluorotoluene (40.0 g, 0.212 mol) was heated at 90° C. in H$_2$O (200 mL)-pyridine (200 mL) with mechanical stirring under Ar. Potassium permanganate (KMnO$_4$) (67 g, 0.424 mol) was added portionwise over 3 h. After 4 h, an HPLC of a filtered sample indicated 50% conversion to the acid. An additional 30 g of KMnO$_4$ was added and heating continued overnight. HPLC indicated 81% conversion. Further KMnO$_4$ was added portionwise with reaction monitoring by HPLC until >95% conversion was obtained. The reaction mixture was filtered through Celite, the filter pad washed with H$_2$O, aq NaOH and EtOH. The filtrate was concentrated to a small volume, then partitioned between 3N NaOH solution and diethyl ether. The aqueous basic layer was separated, cooled in an ice-H$_2$O bath and acidified slowly with 6N HCl solution to precipitate the white solid product. This was collected by suction filtration and dried at 40° C. in a vacuum oven overnight to give the title compound. mp 190–192° C.
$^1$H NMR (CDCl$_3$) δ 7.83 (dd, 1H, J=2, 9 Hz), 7.78 (dd, 1H, J=2, 8 Hz), 7.67–7.71 (m, 1H).

Step B: Preparation of 4-bromo-3-fluorobenzyl Alcohol

4-Bromo-3-fluorobenzoic acid (40.8 g, 0.187 mol) was dissolved in THF (250 ml) with magnetic stirring under Ar in an ice-H$_2$O bath. The cloudy solution was treated dropwise with borane-THF complex (1M) (374 mL, 0.374 mol) over a 1 h period maintaining the internal temperature at <10° C. The reaction mixture was left to warm to ambient temperature overnight, then cooled in an ice-H$_2$O bath and treated dropwise with H$_2$O (150 mL). The THF was removed on a rotary evaporator, and the residue partitioned between EtOAc and H$_2$O. The aqueous layer was extracted with EtOAc (3×100 mL), the organic layers combined, washed with brine, and dried (Na$_2$SO$_4$), filtered, and concentrated to give the title compound as an oil which solidified on standing.
$^1$H NMR (CDCl$_3$) δ 7.52 (t, 1H, J=8 Hz), 7.16 (d, 1H, J=9 Hz), 7.02 (d, 1H, J=8 Hz), 4.67 (s, 2H), 1.47 (br s, 1H).

Step C: Preparation of 2-fluoro-4-hydroxymethylbenzonitrile

4-Bromo-3-fluorobenzyl alcohol (20 g, 0.097 mol) was dissolved in DMF (100 mL) then placed under high vacuum for 15 min. The solution was then purged with Ar for 15 min. While purging continued, zinc cyanide (8 g, 0.068 mol) and the catalyst, Pd[(PPh$_3$)]$_4$, (5.63 g, 0.0049 mol) were added. The reaction mixture was heated at 95° C. under Ar for 18 h, then cooled to ambient temperature and added to H$_2$O. The mixture was extracted with EtOAc, then washed with 1M HCl, H$_2$O, brine, and dried (Na$_2$SO$_4$). Filtration and concentration to dryness gave the title compound as a white solid after chromatography (silica gel, hexane: EtOAc, 6.5:3.5).

$^1$H NMR (CDCl$_3$) δ 7.61 (t, 1H, J=8 Hz), 7.23–7.29 (m, 2H), 4.80 (d, 2H, J=6 Hz), 1.93 (t, 1H, J=6 Hz).

Step D: Preparation of 2-Fluoro-4-formylbenzonitrile

2-Fluoro-4-hydroxymethylbenzonitrile (10 g, 0.066 mol) and triethylamine (32.3 mL, 0.231 mol) were dissolved in CH$_2$Cl$_2$ (100 mL)-DMSO (20 mL) at <5° C. with stirring and treated dropwise with a solution of pyridine.SO$_3$ complex (31.5 g, 0.198 mol) in DMSO (70 mL) maintaining the reaction mixture temperature at <10° C. The reaction mixture was stirred at 5° C. for 1 hr after the addition, then at 20° C. for 1 hr, then partitioned between CH$_2$Cl$_2$ and H$_2$O. The organic layer was separated, washed well with H$_2$O, brine, and dried (Na$_2$SO$_4$). Filtration and concentration gave the title compound after purification by chromatography (silica gel, hexane: EtOAc, 3:1).

$^1$H NMR (CDCl$_3$) δ 10.06 (d, 1H, J=2 Hz), 7.86 (dd, 1H, J=5, 8 Hz), 7.798 (dd, 1H, J=1, 8 Hz), 7.728 (dd, 1H, J=1, 8 Hz).

Step E: Preparation of 2-Fluoro-4-[hydroxy-(3-methyl-3H-imidazol-4-yl)-methyl]-benzonitrile 1-Methylimidazole (15.88 mL, 0.199 mol), dissolved in anhydrous THF (500 mL) in flame-dried glassware under Ar, was cooled to −78° C. and treated with n-butyl lithium (1.6M in hexane)(124 mL, 0.199 mol) via syringe. After stirring for 1 hr chlorotriethylsilane (33.4 mL, 0.199 mol) was added and the reaction mixture was left to warm to ambient temperature overnight. The THF was removed in vacuo with gentle warming, and the residue was redissolved in dry THF (500 mL), cooled to −78° C., and treated with sec-butyl lithium (1.3M in cyclohexane) (153 mL, 0.199 mol) dropwise. After 1 hr this solution was cannulated into a solution of 2-fluoro-4-formylbenzonitrile (27 g, 0.181 mol) in THF (200 mL). After 15 min the cooling bath was removed, the mixture was stirred for 2 hr at ambient temperature, then was quenched with saturated NH$_4$Cl solution. After 15 min 10% HCl was added to pH 3. After 0.5 hr the THF was removed in vacuo, the mixture was made basic with solid Na$_2$CO$_3$ and extracted with EtOAc (3×200 mL). The organics were combined, washed with 10% HCl (3×), the aqueous acidic layers combined, made basic with solid Na$_2$CO$_3$, extracted with EtOAc (3×), the organics combined, washed with brine, and dried (MgSO$_4$). Filtration and concentration to dryness gave the title compound.

Step F: Preparation of 2-Fluoro-4-(3-methyl-3H-imidazole-4-carbonyl)-benzonitrile 2-Fluoro-4-[hydroxy-(3-methyl-3H-imidazol-4-yl)-methyl]-benzonitrile (0.655 g, 2.83 mmol) and MnO$_2$ (1.23 g, 14.2 mmol) were stirred in CH$_2$Cl$_2$ (50 mL) and CH$_3$CN (5 mL) for 3 h. The solution was filtered and concentrated to yield the title compound.

Step G: Preparation of N-[(4-cyano-3-fluoro-phenyl)-(3-methyl-3H-imidazol-4-yl)-methylene]-2-methylpropanesulfinamide 2-Fluoro-4-(3-methyl-3H-imidazole-4-carbonyl)-benzonitrile (2.56 g, 11.2 mmol), titanium(IV) ethoxide (7.02 mL, 33.5 mmol) and commercially available (R)-(+)-2-methyl-2-propanesulfinamide (1.35 g, 11.17 mmol) were dissolved in anhydrous THF (100 mL) and heated at 75° C. for 7 days. The solution was cooled, diluted with brine (100 mL), filtered through a celite pad and washed generously with EtOAc and H$_2$O. The filtrate was separated, dried (MgSO$_4$), and purified using SiO$_2$ chromatography (0–3% MeOH/CH$_2$Cl$_2$) to give the title compound.

Step H: Preparation of N-[1-(4-cyano-3-fluoro-phenyl)-1-(3-methyl-3H-imidazol-4-yl)-ethyl]-2-methylpropanesulfinamide N-[(4-Cyano-3-fluoro-phenyl)-(3-methyl-3H-imidazol-4-yl)-methylene]-2-methylpropanesulfinamide (1.50 g, 4.51 mmol) was dissolved in anhydrous THF (30 mL) at 0° C. and treated with a 3.0M solution of MeMgBr (4.50 mL, 13.5 mmol) in Et$_2$O. After 15 min the reaction was quenched with aq. NH$_4$Cl solution, diluted with saturated NaHCO$_3$ solution and extracted with CH$_2$Cl$_2$ (3×). The combined organic layers were dried (MgSO$_4$), filtered, concentrated, and recrystallized from 95% EtOAc/Hexane to give the title compound.

Step I: Preparation of (−)-4-[1-amino-1-(3-methyl-3H-imidazol-4-yl)-ethyl]-2-fluoro-benzonitrile bishydrochloride A cold methanolic HCl solution (50 mL) was added to N-[1-(4-cyano-3-fluoro-phenyl)-1-(3-methyl-3H-imidazol-4-yl)-ethyl]-2-methylpropanesulfinamide (0.880 g, 2.51 mmol) dissolved in MeOH (50 mL) and stirred for 1h at RT. After concentration and trituration with EtOAc the title compound was obtained as a bis HCl salt as confirmed by chiral HPLC.

Using the procedure described above (Steps G, H, and I), but substituting (S)-(−)-2-methyl-2-propanesulfinamide for (R)-(+)-2-methyl-2-propanesulfinamide in Step G, (+)-4-[1-amino-1-(3-methyl-3H-imidazol-4-yl)-ethyl]-2-fluoro-benzonitrile was obtained.

Step J: Preparation of N-[1-(4-Cyano-3-fluoro-phenyl)-1-(3-methyl-3H-imidazol-4-yl)-ethyl]-3-(3-methoxy-phenyl)-propanamide (+)-4-[1-amino-1-(3-methyl-3H-imidazol-4-yl)-ethyl]-2-fluoro-benzonitrile (0.074 g, 0.25 mmol), 3-(3-methoxyphenyl)propionic acid (0.054 g, 0.3 mmol) (K. J. Hwang et al., J. Org. Chem. (1992), 57[4]1262), EDC (0.275 g, 1.2 mmol), HOAT (0.055 g, 0.40 mmol), and triethylamine (0.167 mL, 1.2 mmol) were combined in DMF (3 mL) and stirred under Ar at ambient temperature for 20 hr. The reaction mixture was partitioned between EtOAc (120 mL) and H$_2$O (100 mL), the organic layer separated, washed with dilute NaHCO$_3$ solution, H$_2$O, brine, and dried (MgSO$_4$). Filtration and concentration to dryness gave the title compound.

Step K: Preparation of N-[1-(4-Cyano-3-fluoro-phenyl)-1-(3-methyl-3H-imidazol-4-yl)-ethyl]-3-(3-hydroxy-phenyl)-propanamide BBr$_3$ (1M in CH$_2$Cl$_2$) (4 mL) was added slowly to a solution of N-[1-(4-cyano-3-fluoro-phenyl)-1-(3-methyl-3H-imidazol-4-yl)-ethyl]-3-(3-methoxy-phenyl)-propanamide (0.123 g, 0.25 mmol) in CHCl$_3$ (2 mL) at 0° C. After 10 min the ice bath was removed and the mixture stirred at 20° C. for 20 min. The mixture was cooled to 0° C., quenched with saturated NaHCO$_3$ solution (25 mL), then extracted with EtOAc (3×50 mL). The organic layers were combined, washed with water, brine, dried (Na$_2$SO$_4$), filtered, and concentrated to give the title compound.

FAB MS(M+1) 393

Step L: Preparation of 5-(4-Cyano-8-methyl-10-oxo-2-oxa-9-aza-tricyclo[11.3.1.1$^{3,7}$]octadeca-1(16),3(18),4,6,13(17),14-hexaen-8-yl)-1-methyl-1H-imidazol-1-ium; 2,2,2-trifluoroacetate A solution of N-[1-(4-cyano-3-fluoro-phenyl)-1-(3-methyl-3H-imidazol-4-yl)-ethyl]-3-(3-hydroxy-phenyl)-propanamide (0.101 g, 0.257 mmol) in DMSO (25 mL) was added dropwise to a mixture of Cs$_2$CO$_3$ (0.750 g, 0.750 mmol) in DMSO (10 mL) over a 2 hr period at 70° C. under Ar. The reaction mixture was stirred at 70° C. for 20 hr. The cooled mixture was partitioned between EtOAc (120 mL) and $H_2O$ (120 mL), the aqueous layer washed with EtOAc, the organics combined, washed with $H_2O$, brine, and dried ($Na_2SO_4$). Filtration and concentration to dryness gave the title compound after preparative RPLC on a Gilson preparative LC.

HRMS theoretical: 373.1659; measured: 373.1656.

Example 2

Preparation of 5-(4-Cyano-8-methyl-10-oxo-2-oxa-9-aza-tricyclo[13.3.1.1$^{3,7}$]eicosa-1(18),3(20),4,6,15 (19),16-hexaen-8-yl)-1-methyl-1H-imidazol-1-ium; 2,2,2-trifluoroacetate Step A: Preparation of 3-(3-Methoxyphenyl)propanol 3-(3-Methoxyphenyl)propionic acid (see Example 1, Step J) (10.09 g, 0.058 mol) dissolved in anhydrous THF 60 mL) was added dropwise to a solution of $LiAlH_4$ (1M in THF) (60 mL, 0.06 mol) in THF (60 mL) at ambient temperature under Ar. The resulting solution was stirred at reflux for 6 hr, then cooled to 0° C., treated dropwise with $H_2O$ (2.2 mL), 20% NaOH (1.7 mL), then $H_2O$ (6.62 mL). After stirring for 15 min, $MgSO_4$ was added, stirring was continued for 15 min, the solids were filtered off, washed well with EtOAc, and the filtrate concentrated to dryness to give the title compound. MS (M+1) 167.1

Step B: Preparation of 3-(3-Methoxyphenyl)propylbromide

Allyl bromide (25 mL, 0.28 mmol) was added to a solution of 3-(3-methoxyphenyl)propanol (8.8 g, 0.053 mol), N,N'-carbonyldiimidazole (9.6 g, 0.0605 mol) and $CH_3CN$ (45 mL) at room temperature. After 1.5 hr at rt and 1.5 hr at reflux, the reaction mixture was cooled, partitioned between EtOAc (250 mL) and $H_2O$ (300 mL), the organic layer washed with $H_2O$ (300mL), 5% HCl (200 mL), dilute $NaHCO_3$ solution (200 mL), brine (300 mL), and dried ($Na_2SO_4$). Filtration and concentration to dryness gave the title compound.

Step C: Preparation of 2-[3-(3-Methoxy-phenyl)-propyl]-malonic Acid Diethyl Ester Diethylmalonate (7.65 mL, 0.050 mol) was added slowly to a vigorously stirred suspension of pre-washed NaH (60%) (2.4 g, 0.050 mol) in dry DMF (50 mL) at 0° C. under Ar. After 15 min, 3-(3-methoxyphenyl)propylbromide (11.5 g, 0.050 mol) was added slowly, the ice bath was removed, and the reaction mixture was stirred at 65° C. for 16 hr. The mixture was cooled, partitioned between EtOAc (250 mL) and $H_2O$ (200 mL), the organic layer washed with $H_2O$ (2×500 mL), dried ($Na_2SO_4$), filtered, and concentrated to dryness to give the title compound.
FAB MS(M+1) 309.1

Step D: Preparation of 5-(3-Methoxyphenyl)pentanoic acid

KOH (7.0 g, 0.105 mol) was added slowly to a hot solution of the diester from Step C (14 g, 0.046 mol) in ethylene glycol (50 mL) with stirring under Ar. The reaction mixture was heated at reflux for 3 hr, cooled, acidified to pH=2 with HCl, diluted with $H_2O$ (150 mL), and extracted with benzene (3×50 mL). The organic layers were combined, washed with dilute $NaHCO_3$ solution (2×100 mL), $H_2O$ (2×50 mL), dried, filtered, and concentrated to dryness to give the title compound after chromatography on $SiO_2$ eluting with $CHCl_3$:MeOH, 40:1.
HRMS: theoretical, 226.1438; measured, 226.1435.

Step E: Preparation of 5-(4-Cyano-8-methyl-10-oxo-2-oxa-9-aza-tricyclo[13.3.1.1$^{3,7}$]eicosa-1(18),3(20),4,6,15(19), 16-hexaen-8-yl)-1-methyl-1H-imidazol-1-ium; 2,2,2-trifluoroacetate Following the procedures described in Example 1, Steps J, K and L but substituting 5-(3-methoxyphenyl)pentanoic acid for 3-(3-methoxyphenyl)propionic acid, the title compound was prepared.
HRMS: theoretical, 401.1972; measured, 401.1951.

Example 3

Preparation of 5-(4-Cyano-8-methyl-10-oxo-2-oxa-9-aza-tricyclo[15.3.1.1$^{3,7}$]docosa-1(20),3(22),4,6,17 (21),18-hexaen-8-yl)-1-methyl-1H-imidazol-1-ium; 2,2,2-trifluoroacetate Using the procedures described in Example 2, but substituting 5-(3-methoxyphenyl)pentanoic acid (Example 2, Step D) for 5-(3-methoxyphenyl) propionic acid in Step A, the title compound was prepared.
HRMS: theoretical, 429.2285; measured, 429.2283.

Example 4

Preparation of 5-(4-Cyano-8-methyl-10-oxo-2-oxa-9-aza-(16-spiro-(2-cyclohexanone) tricyclo [15.3.1.1$^{3,7}$]docosa-1(20),3(22),4,6,17(21),18-hexaen-8-yl)-1-methyl-1H-imidazol-1-ium 2,2,2-trifluoroacetate

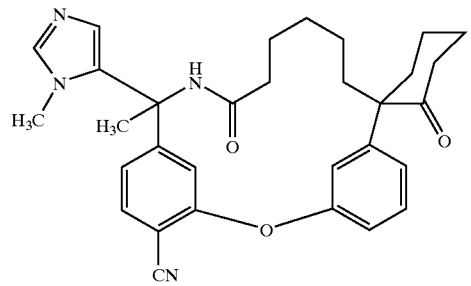

Step A: Preparation of 5-[1-(3-Methoxy-phenyl)-2-oxo-cyclohexyl]-pentanoic Acid Ethyl Ester 2-(3-Methoxy-phenyl)-cyclohexanone (0.80 g, 4.05 mmol) was added slowly to a suspension of NaH (60%) (0.185 g, 5.1 mmol) in anhydrous DMF (5 mL) at 0° C. under Ar over 15 min. After an additional 15 min. at 20° C. 6-bromohexanoic acid ethyl ester (1.0 g, 4.5 mmol) was added followed by stirring at 60° C. for 6 hr. The reaction mixture was cooled, quenched with saturated $NH_4Cl$ solution, partitioned between EtOAc (150 mL) and $H_2O$ (100 mL), the organic layer washed with $H_2O$ (2×100 mL), dried ($Na_2SO_4$), filtered, and concentrated to dryness to give the title compound after silica gel chromatography eluting with hexane:EtOAc, 50:1 to 10:1.

Step B: Preparation of 5-[1-(3-Methoxy-phenyl)-2-oxo-cyclohexyl]-pentanoic Acid

Solid KOH (0.090 g, 1.4 mmol) was added to a solution of the ester from Step A (0.132 g, 0.38 mmol) in EtOH (5 mL). After stirring at ambient temperature for 48 hr, the reaction mixture was partitioned between EtOAc (50 mL) and $H_2O$ (100 mL), the aqueous layer acidified, then extracted with EtOAc (2×100 mL), the organic layer washed with $H_2O$ (50 mL), dried ($Na_2SO_4$), filtered, and concentrated to dryness to give the title compound. Mp 89–91° C. MS 318.

Step C: Preparation of 5-(4-Cyano-8-methyl-10-oxo-2-oxa-9-aza-16-spiro(2-cyclohexanone) tricyclo[15.3.1.1$^{3,7}$] docosa-1(20),3(22),4,6,17(21),18-hexaen-8-yl)-1-methyl-1H-imidazol-1-ium; 2,2,2-trifluoroacetate Using the procedures described in Example 1, Steps J, K and L, but substituting 5-[1-(3-methoxy-phenyl)-2-oxo-cyclohexyl]-pentanoic acid from Step B above for 3-(3-methoxyphenyl) propionic acid in Step J, the title compound was prepared.
HRMS: theoretical, 511.2704; measured, 511.2692.

The other enantiomer of 5-(4-Cyano-8-methyl-10-oxo-2-oxa-9-aza-16-spiro (2-cyclohexanone) tricyclo[15.3.1.1$^{3,7}$] docosa-1(20),3(22),4,6,17(21),18-hexaen-8-yl)-1-methyl-1H-imidazol-1-ium; 2,2,2-trifluoroacetate was prepared using (−)-4-[1-amino-1-(3-methyl-3H-imidazol-4-yl)-ethyl]-2-fluoro-benzonitrile bishydrochloride from Example 1, Step I.
HRMS: theoretical, 511.2704; measured, 511.2701.

Example 5

Preparation of 14-Amino-14-(3-methyl-3H-imidazol-4-yl)-2,9-dioxa-tricyclo[13.3.1.1$^{3,7}$]eicosa-1(18),3,5,7(20),15(19),16-hexaene-18-carbonitrile Step A: Preparation of 3-tert-butoxy-benzoic Acid Ethyl Ester Into a solution of 3-hydroxy-benzoic acid ethyl ester (10.14 g, 0.061 mol) in $CH_2Cl_2$ (200 mL) cooled to −78° C. was condensed isobutylene (150 mL) followed by addition of triflic acid (1.08 mL, 0.061 mol). The reaction mixture was allowed to warm to −20° C. When a solution was obtained and tlc indicated loss of starting material, the reaction was quenched with $Et_3N$ (6.8 mL, 0.049 mol) and left to warm to ambient temperature. The solution was concentrated and the residue chromatographed on an ISCO combiflash eluting with 0–10% EtoAc/hexane to give 12.91 g (95%) of the title compound.
$^1$H NMR (CDCl$_3$) δ 7.76 (d, 1H, J=8 Hz), 7.66 (s, 1H), 7.33 (t, 1H, J=8 Hz), 7.26 (s, 1H), 7.18 (dd, 1H, J=2, 8 Hz), 4.37 (q, 2H, J=7 Hz), 1.39 (t, 3H, J=7 Hz, 1.37 (s, 9H).

Step B: Preparation of (3-tert-butoxy-phenyl) Methanol

To a suspension of LiAlH$_4$ (1.707 g, 0.045 mol) in anhydrous diethyl ether (80 mL) in a 3-necked rb flask equipped with addition funnel at 0° C. in an ice-water bath was added dropwise a solution of 3-tert-butoxy-benzoic acid ethyl ester (5.0 g, 0.0225 mol) in ether (20 mL). The reaction mixture was left to warm to rt over 15 min, then cooled in an ice-water bath and quenched by dropwise addition of $H_2O$. The mixture was partitioned between ether and $H_2O$, the aqueous layer washed with ether (2×30 mL), the organics combined, washed with brine, dried (MgSO$_4$), filtered and concentrated to give 3.70 g (82%) of the title compound.
$^1$H NMR (CDCl$_3$) δ 7.23–7.27 (m, 1H), 7.07 (d, 1H, J=8 Hz), 7.00 (s, 1H), 6.92 (d, 1H, J=8 Hz), 4.66 (d, 2H, J=5 Hz), 1.69 (t, 1H, J=5 Hz), 1.35 (s, 9H).

Step C: Preparation of 1-(4-bromo-butoxymethyl)-3-tert-butoxy-benzene

To a solution of (3-tert-butoxy-phenyl) methanol (4.02 g, 0.022 mol) and tetrabutylammonium hydrogen sulfate (0.379 g, 0.00115 mol) in 50% NaOH solution (6 mL) and benzene (15 mL) Was added 1,4-dibromobutane (7.99 mL, 0.067 mol) with vigorous stirring at ambient temperature. After stirring for 8 h, the mixture was partitioned between $H_2O$ and EtOAc. The organic layer was separated, washed with brine, dried (MgSO$_4$), filtered, and concentrated to give the title compound after purification on an ISCO Combiflash eluting with 0–10% EtOAc/hexane.
$^1$H NMR (CDCl$_3$) δ 7.23 (t, 1H, J=8 Hz), 7.03 (d, 1H, J=8 Hz), 6.96 (s, 1H), 6.91 (dd, 1H, J=1, 8 Hz), 4.47 (s, 2H), 3.48 (t, 1H, J=6 Hz), 3.43 (t, 1H, J=6 Hz), 1.94–2.01 (m, 2H), 1.72–1.79 (m, 2H), 1.35 (s, 9H).

Step D: Preparation of 2-methyl-propane-2-sulfinic acid [5-(3-tert-butoxy-benzyloxy)-1-(4-cyano-3-fluoro-phenyl)-1-(3-methyl-3H-imidazol-4-yl)-pentyl]-amide Magnesium (0.09 g, 3.61 mmol) was flame dried in a 50 mL RB flask equipped with addition funnel and magnetic stirrer under $N_2$. When the flask had cooled, anhydrous THF (3 mL), a pinch of iodine, and a THF solution of Rieke magnesium (1 mL) were added, followed by a small portion of 1-(4-bromo-butoxymethyl)-3-tert-butoxy-benzene (1.134 g, 3.61 mmol) in THF (5 mL) with slight warming to initiate the reaction. The remainder of the bromide solution was added dropwise over 15 min. After 15 min. this Grignard solution was added to a solution of N-[(4-cyano-3-fluoro-phenyl)-(3-methyl-3H-imidazol-4-yl)-methylene]-2-methylpropanesulfinamide (Example 1, Step G) (0.30 g, 0.90 mmol) in THF (5 mL) with cooling in an ice-$H_2O$ bath. After 5 mL of Grignard solution was consumed, the reaction was complete by HPLC. The reaction mixture was quenched with $H_2O$, diluted with saturated NaHCO$_3$ solution and extracted with $CH_2Cl_2$ (2×20 mL). The organic layers were combined, washed with brine, dried (MgSO$_4$), filtered and concentrated to give the crude product. Purification by RP LC on a Delta Prep Pak eluting with 95:5 to 5:95 $H_2O$ (0.1% TFA): CH$_3$CN(0.1% TFA) gave both diastereomers in a 3.5:1 ratio after concentration of the fractions followed by a toluene azeotrope. MS (M+1) 569 for both diastereomers A and B.

Step E: Preparation of 4-[1-amino-5-(3-hydroxy-benzyloxy)-1-(3-methyl-3H-imidazol-4-yl)-pentyl]-2-fluoro-benzonitrile 2-Methyl-propane-2-sulfinic acid [5-(3-tert-butoxy-benzyloxy)-1-(4-cyano-3-fluoro-phenyl)-1-(3-methyl-3H-imidazol-4-yl)-pentyl]-amide (A) (0.396 g, 0.58 mmol) was dissolved in methanol (15 mL) and treated with 4M HCl in dioxane (9 mL). After 1 h, the reaction mixture was concentrated in vacuo, azeotroped with $CH_2Cl_2$ (3×), rinsed with $CH_2Cl_2$, and the solid collected to give enantiomer A of the title compound. MS (M+1) 409. Using the same procedure, diastereomer B (Step D) (0.110 g, 0.161 mmol) gave enantiomer B of the title compound.

Step F: Preparation of 14-Amino-14-(3-methyl-3H-imidazol-4-yl)-2,9-dioxa-tricyclo[13.3.1.1$^{3,7}$]eicosa-1(18),3,5,7(20),15(19),16-hexaene-18-carbonitrile 4-[1-Amino-5-(3-hydroxy-benzyloxy)-1-(3-methyl-3H-imidazol-4-yl)-pentyl]-2-fluoro-benzonitrile (0.214 g, 0.443 mmol) was dissolved in DMF (44 mL) at ambient temperature and treated with Cs$_2$CO$_3$ (0.577 g, 1.77 mmol). After 18 h, the reaction mixture was concentrated to dryness, and partitioned between a minimum amount of $H_2O$ and $CH_2Cl_2$. The aqueous layer was washed with $CH_2Cl_2$ (2×), the organics combined, dried (MgSO$_4$), filtered and concentrated to give the title compound after purification on the ISCO Combiflash eluting with 1–3% MeOH/$CH_2Cl_2$w/NH$_4$OH. MS (M+1) 389.
Anal. Calculated for $C_{23}H_{24}N_4O_2$.0.3 $H_2O$: C, 70.14; H, 6.30; N, 14.22; Found: C, 70.04; H, 6.29; N, 13.97.
Using the same procedure but substituting enantiomer B from Step E, the other enantiomer of 14-amino-14-(3-methyl-3H-imidazol-4-yl)-2,9-dioxa-tricyclo[13.3.1.1$^{3,7}$] eicosa-1(18),3,5,7(20),15(19),16-hexaene-18-carbonitrile was prepared. MS (M+1) 389.
Anal. Calculated for $C_{23}H_{24}N_4O_2$.0.1 $H_2O$: C, 70.78; H, 6.25; N, 14.36; Found: C, 70.62; H, 6.31; N, 14.49.

Example 6

Preparation of 15-Amino-15-(3-methyl-3H-imidazol-4-yl)-2,9-dioxa-tricyclo[14.3.1.1$^{3,7}$] heneicosa-1(20),3,5,7(21),16.18-hexaene-19-carbonitrile Using the procedures described in Example 5, but substituting 1,5-dibromopentane for 1,4-dibromobutane in Step C, the title compound was prepared.
MS (M+1) 403.

Example 7

Preparation of 14-amino-14-(3-methyl-3H-imidazol-4-yl)-2-oxa-10-aza-tricyclo[13.3.1.1$^{3,7}$]eicosa-1(18), 3,5,7(20), 15(19),16-hexaene-18-carbonitrile Step A: Preparation of 2-methyl-propane-2-sulfinic acid [4-tert-butyl-dimethyl-silanyloxy)-1-(4-cyano-3-fluoro-phenyl)-1-(3-methyl-3H-imidazol-4-yl)-butyl]-amide Magnesium (0.317 g, 12.03 mmol) was flame dried in a 50 mL RB flask equipped with addition funnel and magnetic stirrer under N$_2$. When the flask had cooled, anhydrous THF (3 mL), a pinch of iodine, and a THF solution of Rieke magnesium (1 mL) were added, followed by a small portion of (3-bromopropoxy)-tert-butyldimethylsilane (3.048 g, 12.03 mmol) in THF (5 mL) with slight warming to initiate the reaction. The remainder of the bromide solution was added dropwise over 15 min. After 15 min. this Grignard solution was added to a solution of N-[(4-cyano-3-fluoro-phenyl)-(3-methyl-3H-imidazol-4-yl)-methylene]-2-methylpropanesulfinamide (Example 1, Step G) (1.00 g, 3.01 mmol) in THF (5 mL) with cooling in an ice-H$_2$O bath. After 5 mL of Grignard solution was consumed, the reaction was complete by HPLC. The reaction mixture was quenched with H$_2$O, diluted with saturated NaHCO$_3$ solution and extracted with CH$_2$Cl$_2$ (2×20 mL). The organic layers were combined, washed with brine, dried (MgSO$_4$), filtered and concentrated to give the crude product. Purification on an ISCO Combiflash eluting with 1–3% MeOH/CH$_2$Cl$_2$ w/NH$_4$OH gave the title compound.

Step B: Preparation of 2-methyl-propane-2-sulfinic acid [4-hydroxy)-1-(4-cyano-3-fluoro-phenyl)-1-(3-methyl-3H-imidazol-4-yl)-butyl]-amide 2-Methyl-propane-2-sulfinic acid [4-tert-butyl-dimethyl-silanyloxy)-1-(4-cyano-3-fluoro-phenyl)-1-(3-methyl-3H-imidazol-4-yl)-butyl]-amide (0.84 g, 1.66 mmol) was dissolved in THF (15 mL), treated with tetrabutylammonium fluoride and stirred at ambient temperature for 0.5 h. The mixture was partitioned between CH$_2$Cl$_2$ and aqueous saturated NaHCO$_3$ solution, the aqueous layer washed with CH$_2$Cl$_2$ (3×20 mL), the organic layers combined, washed with brine and dried (MgSO$_4$). Filtration and concentration gave the title compound after chromatography on an ISCO Combiflash eluting with 2–6% MeOH/CH$_2$Cl$_2$ w/NH$_4$OH. MS (M+1) 393.

Step C: Preparation of 2-methyl-propane-2-sulfinic acid [1-(4-cyano-3-fluoro-phenyl)-4-[2-(3-methoxy-phenyl)-ethylamino]-1-(3-methyl-3-H-imidazol-4-yl)-butyl]-amide 2-Methyl-propane-2-sulfinic acid [4-hydroxy)-1-(4-cyano-3-fluoro-phenyl)-1-(3-methyl-3H-imidazol-4-yl)-butyl]-amide (0.025 g, 0.0637 mmol) was dissolved in anhydrous CH$_2$Cl$_2$ (3 mL) at ambient temperature, then treated with the Dess-Martin periodate (0.058 mL, 0.596 mmol). After 0.5 h, the reaction mixture was partitioned between CH$_2$Cl$_2$ and saturated NaHCO$_3$ solution, the aqueous layer separated, washed with CH$_2$Cl$_2$ (3×), the organics combined and dried (MgSO$_4$). Filtration and concentration gave crude aldehyde that was dissolved in MeOH (5 mL). 3-Methoxy-phenethylamine (0.0093 mL, 0.0637 mmol) was added, the pH adjusted to 5 with acetic acid, then NaCNBH$_3$ (0.006 g, 0.0956 mmol) added, and the mixture was stirred at for 18 h. The crude product was purified by RP LC on a Delta PrepPak eluting with 95:5 to 5:95 H$_2$O (0.1% TFA): CH$_3$CN(0.1% TFA) to give the title compound. MS (M+1) 526.

Step D: Preparation of 4-[1-amino-4-[2-(3-hydroxy-phenyl)-ethylamino]-1-(3-methyl-3H-imidazol-4-yl)-butyl]-2-fluoro-benzonitrile 2-Methyl-propane-2-sulfinic acid [1-(4-cyano-3-fluoro-phenyl)-4-[2-(3-methoxy-phenyl)-ethylamino]-1-(3-methyl-3-H-imidazol-4-yl)-butyl]-amide (0.075 g, 0.1427 mmol) was dissolved in CH$_2$Cl$_2$ (7 mL) with cooling in an ice-H$_2$O bath, then treated with BBr$_3$ (1 mL of a 1M solution in CH$_2$Cl$_2$, 1 mmol). After 15 min., H$_2$O (3 mL) was added and the reaction mixture was concentrated in vacuo. The residue was dissolved in MeOH and stirred at ambient temperature for 15 min. Concentration to dryness gave the title compound which was used without further purification. MS (M+1) 408.

Step E: Preparation of 14-amino-14-(3-methyl-3H-imidazol-4-yl)-2-oxa-10-aza-tricyclo[13.3.1.1$^{3,7}$]eicosa-1(18),3,5,7(20),15(19),16-hexaene-18-carbonitrile 4-[1-Amino-4-[2-(3-hydroxy-phenyl)-ethylamino]-1-(3-methyl-3H-imidazol-4-yl)-butyl]-2-fluoro-benzonitrile (0.058 g, 0.142 mmol) was dissolved in DMF (15 mL) and treated with Cs$_2$CO$_3$ (0.324 g, 0.994 mmol). After 18 h at 60° C., the reaction mixture was concentrated in vacuo, dissolved in H$_2$O: 0.1% TFA (3 mL) and purified by RP LC on a Delta PrepPak eluting with 95:5 to 5:95 H$_2$O (0.1% TFA): CH$_3$CN(0.1% TFA) to give the title compound as an 80:20 mixture of enantiomers.

MS (M+1) 388.

Example 8

In vitro Inhibition of Ras Farnesyl Transferase

Transferase Assays. Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 mM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor IC$_{50}$ determinations are as follows: FTase, 650 nM Ras-CVLS (SEQ.ID.NO.: 1), 100 nM farnesyl diphosphate.

The compounds of the instant invention are tested for inhibitory activity against human FPTase by the assay described above.

The compounds of the instant invention described in the above Examples 1–7 were tested for inhibitory activity against human FPTase by the assay described above and were found to have an IC$_{50}$ of ≦5 μM.

Example 9

Modified in vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5mM ATP), 5 mM $MgCl_2$, 10 $\mu$M $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 $\mu$L of a 3 mg/mL suspension of streptavidin SPA beads (Scintillation Proximity Assay beads, Amersham) in 0.2M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near KM concentrations. Enzyme and substrate concentrations for inhibitor $IC_{50}$ determinations are as follows: 75 pM GGTase-I, 1.6 $\mu$M Ras peptide, 100 nM geranylgeranyl diphosphate.

The compounds of the instant invention are tested for inhibitory activity against human GGTase-type I by the assay described above.

Example 10
Cell-Based in vitro Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 $\mu$Ci[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 $\mu$l of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/ 0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 11
Cell-Based in vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 12
Construction of SEAP Reporter Plasmid pDSE 100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796-1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

intron A sequence was mutated at nucleotide 1856 (nucleotide numbering as in Chapman, B. S., Thayer, R. M., Vincent, K. A. and Haigwood, N. L., Nuc. Acids Res. 19, 3979-3986) to remove a SacI restriction site using site directed mutagenesis. The mutated intron A sequence was PCRed from the plasmid p16T-287 using the following oligos.

```
Sense strand:
5' GGCAGAGCTCGTTTAGTGAACCGTCAG 3'        (SEQ.ID.NO.:8)

Antisense strand:
5' GAGAGATCTCAAGGACGGTGACTGCAG 3'        (SEQ.ID.NO.:9)
```

```
Sense strand       5' GAGAGGGAATTCGGGCCCTTCCTGCATGCTGCTGCTGCTGCTGCTGGGC 3'   (SEQ.ID.NO.:4)
N-terminal SEAP:

Antisense strand  5' GAGAGAGCTCGAGGTTAACCCGGGTGCGCGGCGTCGGTGGT 3'            (SEQ.ID.NO.:5)
N-terminal SEAP:

Sense strand       5' GAGAGAGTCTAGAGTTAACCCGTGGTCCCCGCGTTGCTTCCT 3'           (SEQ.ID.NO.:6)
C-terminal SEAP:

Antisense strand  5' GAAGAGGAAGCTTGGTACCGCCACTGGGCTGTAGGTGGTGGCT 3'           (SEQ.ID.NO.:7)
C-terminal SEAP:
```

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 5) introduces an internal translation STOP codon within the SEAP gene along with the HpaI site. The C-terminal oligos (SEQ.ID.NO.: 6 and SEQ.ID.NO.: 7) were used to amplify a 412 bp C-terminal PCR product containing HpaI and HindIII restriction sites. The sense strand C-terminal oligo (SEQ.ID.NO.: 6) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electro-phoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid PCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf(−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on Aug. 27, 1998, and designated ATCC), contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative Construction of a Constitutively Expressing SEAP Plasmid pCMV-SEAP-B An expression plasmid constitutively expressing the SEAP protein can be created by placing the sequence encoding a truncated SEAP gene downstream of the cytomegalovirus (CMV) IE-I promoter and upstream of the 3' unstranslated region of the bovine growth hormone gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into *E. coli* DH5α cells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated Viral-H-ras Expression Plasmid pSMS600

A DNA fragment containing viral-H-ras can be PCRed from plasmid "HB-11" (deposited in the ATCC under Budapest Treaty on Aug. 27, 1997, and designated ATCC 209,218) using the following oligos.

```
                                          (SEQ.ID.NO.:10)
Sense strand:
5'TCTCCTCGAGGCCACCATGGGGAGTAGCAAGAGCAAGCCTAAGGACCC

CAGCCAGCGCCGGATGACAGAATACAAGCTTGTGGTGG3'.
```

```
                                          (SEQ.ID.NO.:11)
Antisense:
5'CACATCTAGATCAGGACAGCACAGACTTGCAGC3'.
```

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid, pSMS600, in which the recombinant myr-viral-H-ras gene is constitutively transcribed from the CMV promoter of the pCI vector.

Cloning of a Viral-H-ras-CVLL Expression Plasmid pSMS601

A viral-H-ras clone with a C-terminal sequence encoding the amino acids CVLL can be cloned from the plasmid "HB-11" by PCR using the following oligos.

```
                                          (SEQ.ID.NO.:12)
Sense strand:
5'TCTCCTCGAGGCCACCATGACAGAATACAAGCTTGTGGTGG-3'
```

```
                                          (SEQ.ID.NO.:13)
Antisense strand:
5'CACTCTAGACTGGTGTCAGAGCAGCACACACTTGCAGC-3'
```

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of Cellular-H-ras-Leu61 Expression Plasmid pSMS620

The human cellular-H-ras gene can be PCRed from a human cerebral cortex cDNA library (Clontech) using the following oligonucleotide primers.

```
                                          (SEQ.ID.NO.:14)
Sense strand
5'-GAGAGAATTCGCCACCATGACGGAATATAAGCTGGTGG-3'
```

```
                                          (SEQ.ID.NO.:15)
Antisense strand:
5'-GAGAGTCGACGCGTCAGGAGAGCACACACTTGC-3'
```

The primers will amplify a c-H-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

```
5'-CCGCCGGCCTGGAGGAGTACAG-3'       (SEQ.ID.NO.:16)
```

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid, pSMS620, will constitutively transcribe c-H-ras-Leu61 from the CMV promoter of the pCI vector.

Cloning of a c-N-ras-Val-12 Expression Plasmid pSMS630

The human c-N-ras gene can be PCRed from a human cerebral cortex cDNA library (Clontech) using the following oligonucleotide primers.

Sense strand: (SEQ.ID.NO.:17)
5'-GAGAGAATTCGCCACCATGACTGAGTACAAACTGGTGG-3'

Antisense strand: (SEQ.ID.NO.:18)
5'-GAGAGTCGACTTGTTACATCACCACACATGGC-3'

The primers will amplify a c-N-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.:19)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid, pSMS630, will constitutively transcribe c-N-ras-Val-12 from the CMV promoter of the pCI vector.

Cloning of a c-K4B-ras-Val-12 Expression Plasmid pSMS640

The human c-K4B-ras gene can be PCRed from a human cerebral cortex cDNA library (Clontech) using the following oligo-nucleotide primers.

Sense strand: (SEQ.ID.NO.:20)
5'-GAGAGGTACCGCCACCATGACTGAATATAAACTTGTGG-3'

Antisense strand: (SEQ.ID.NO.:21)
5'-CTCTGTCGACGTATTTACATAATTACACACTTTGTC-3'

The primers will amplify a c-K4B-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K4B-ras fragment can be ligated into a KpnI -Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.:22)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 Expression Plasmid pSMS650

The human c-K4A-ras gene can be PCRed from a human cerebral cortex cDNA library (Clontech) using the following oligo-nucleotide primers.

Sense strand: (SEQ.ID.NO.:23)
5'-GAGAGGTACCGCCACCATGACTGAATATAAACTTGTGG-3'

Antisense strand: (SEQ.ID.NO.:24)
5'-CTCTGTCGACAGATTACATTATAATGCATTTTTTAATTTTCACAC-3'

The primers will amplify a c-K4A-Ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras4A fragment can be ligated into a KpnI -Sal I cut mutagenesis vector pAlter-1(Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.:25)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP Assay

Human $C_{33}A$ cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 μl of $CaCl_2$-DNA solution is added dropwise while vortexing to 600 μl of 2× HBS buffer to give 1.2 ml of precipitate solution (see recipes below). This is allowed to sit at room temperature for 20 to 30 minutes. While the precipitate is forming, the media on the $C_{33}A$ cells is replaced with DMEM (minus phenol red; Gibco cat. No. 31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 μl/well) to which drug, diluted in media, has already been added in a volume of 100 μl. The final volume per well is 200 μl with each drug concentration repeated in triplicate over a range of half-log steps.

Incubation of cells and drugs is for 36 hrs at 37° under $CO_2$. At the end of the incubation period, cells are examined micro-scopically for evidence of cell distress. Next, 100 μl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 μl media is combined with 200 μl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-CaPO$_4$ precipitate for 10 cm. plate of cells | |
|---|---|
| Ras expression plasmid (1 μg/μl) | 10 μl |
| DSE-SEAP Plasmid (1 μg/μl) | 2 μl |
| Sheared Calf Thymus DNA (1 μg/μl) | 8 μl |
| 2M CaCl$_2$ | 74 μl |
| dH$_2$O | 506 μl |
| 2X HBS Buffer | |
| 28O mM NaCl | |
| 10 mM KCl | |
| 1.5 mM Na$_2$HPO$_4$2H$_2$0 | |
| 12 mM dextrose | |
| 50 mM HEPES | |
| Final pH = 7.05 | |
| Luminesence Buffer (26 ml) | |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer
Add 0.05M Na$_2$CO$_3$ to 0.05M NaHCO$_3$ to obtain pH 9.5. Make 1 mM in MgCl$_2$ Example 13
The Processing Assays Employed are Modifications of that Sescribed by DeClue et al [Cancer Research 51, 712–717, 1991].
K4B-Ras Processing Inhibition Assay PSN-1(human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 μM), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 μCi/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 μg/ml AEBSF, 10 μg/ml aprotinin, 2 μg/ml leupeptin and 2 μg/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 μg of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 μl elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 μg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% CO$_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. # MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and EC$_{50}$ values are generated using 4-parameter curve fits in SigmaPlot software.

Example 14
Rap1 Processing Inhibition Assay
Protocol A:
Cells are labeled, incubated and lysed as described in Example 10.
For immunoprecipitation of Rap I, samples of lysate supernatant containing equal amounts of protein are utilized.

Protein concentration is determined by the bradford method utilizing bovine serum albumin as a standard. The appropriate volume of lysate is brought to 1 ml with lysis buffer lacking DTT and 2 μg of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 μl elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 μg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1× Pen/Strep antibiotic mix. The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1–100 μM. Four concentrations per compound is typical. The compounds are diluted so that each concentration is 1000× of the final concentration (i.e., for a 10 μM data point, a 10 mM stock of the compound is needed).

2 μL of each 1000× compound stock is diluted into 1 ml media to produce a 2×stock of compound. A vehicle control solution (2 ,L DMSO to 1 ml media), is utilized. 0.5 ml of the 2×stocks of compound are added to the cells.

After 24 hours, the media is aspirated from the assay plates. Each well is rinsed with 1 ml PBS, and the PBS is aspirated. 180 μL SDS-PAGE sample buffer (Novex) containing 5% 2-mercapto-ethanol is added to each well. The plates are heated to 100° C. for 5 minutes using a heat block containing an adapter for assay plates. The plates are placed on ice. After 10 minutes, 20 μL of an RNAse/DNase mix is added per well. This mix is 1 mg/ml DNaseI (Worthington Enzymes), 0.25 mg/ml Rnase A (Worthington Enzymes), 0.5M Tris-HCl pH 8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS +0.1% Tween-20). If blocked over the weekend, 0.02% sodium azide is added. The membranes are blocked at 4° C. with slow rocking.

The blocking solution is discarded and 20ml fresh blocking solution containing the anti Rap1a antibody (Santa Cruz Biochemical SC 1482) at 1:1000 (diluted in Western blocking buffer) and the anti Rab6 antibody (Santa Cruz Biochemical $SC_{310}$) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C:

This protocol allows the determination of an $EC_{50}$ for inhibition of processing of Rap1a. The assay is run as described in Protocol B with the following modifications. 20 μl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121;Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant□ software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 15

In vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of the formula A1:

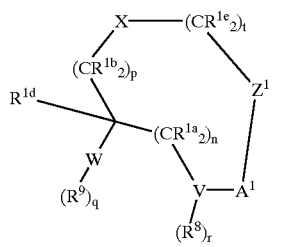

A1 wherein:

$R^{1a}$, $R^{1b}$, $R^{1d}$ and $R^{1e}$ are independently selected from:
 a) hydrogen,
 b) unsubstituted or substituted aryl, unsubstituted or substituted heterocycle, $C_3$–$C_{10}$ cycloalkyl, $C_1$–$C_6$ perfluoroalkyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $(R^{10})_2N$—$C(O)NR^{10}$—, $R^{10}C(O)$—, $R^{10}OC(O)$—, —$N(R^{10})_2$, or $R^{10}OC(O)NR^{10}$—,
 c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$—$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, $C_1$–$C_6$ perfluoroalkyl, halogen, $R^{10}O$—, $R^4S(O)_m$—, $R^4S(O)_2NR^{10}$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, —$N(R^{10})_2$, and $R^{11}OC(O)$—$NR^{10}$—;

or two $R^{1a}$s, two $R^{1b}$s or two $R^{1e}$s, on the same carbon atom may be combined to form —$(CH_2)_v$—, wherein one of the $CH_2$ moieties is optionally replaced with —$C(=O)$—, —NH— or —$NHC(=O)$—;

$R^4$ is selected from $C_{1-4}$ alkyl, $C_{3-6}$ cycloalkyl, heterocycle, aryl, unsubstituted or substituted with:
 a) $C_{1-4}$ alkoxy,
 b) aryl or heterocycle,
 c) halogen,
 d) HO,
 e)

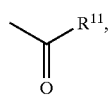

f) —$SO_2R^{11}$,
 g) $N(R^{10})_2$, or
 h) $C_{1-4}$ perfluoroalkyl;

$R^6$ and $R^7$ are independently selected from:
 1) hydrogen,
 2) $R^{10}C(O)$—, or $R^{10}OC(O)$—, and
 3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, unsubstituted or substituted with one or more substituents selected from:
  a) $R^{10}O$—,
  b) aryl or heterocycle,
  c) halogen,
  d) $R^{10}C(O)NR^{10}$—,
  e)

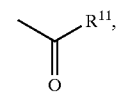

f) —$SO_2R^{11}$,
  g) $N(R^{10})_2$,
  h) $C_{3-6}$ cycloalkyl,
  i) $C_1$–$C_6$ perfluoroalkyl,
  j) $(R^{10})_2N$—$C(NR^{10})$—,
  k) $R^{10}OC(O)$—,
  l) $R^{11}OC(O)NR^{10}$—,
  m) CN, and
  n) $NO_2$, or $R^6$ and $R^7$ may be joined in a ring;

$R^8$ is independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $R^{10}OC(O)$—, —$N(R^{10})_2$, or $R^{11}OC(O)NR^{10}$—, and
 c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$, $R^{11}S(O)_m$—, $R^{10}C(O)NH$—, $(R^{10})_2NC(O)$—, $R^{10})_2N$—$C(NR^{10})$—, CN, $R^{10}C(O)$—, $R^{10}OC(O)$—, —$N(R^{10})_2$, or $R^{10}OC(O)NH$—;

$R^9$ is selected from:
 a) hydrogen,
 b) $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10})_2NC(NR^{10})$—, CN, $NO_2$, $R^{10}C(O)$—, $R^{10}OC(O)$—, —$N(R^{10})_2$, or $R^{11}OC(O)NR^{10}$—, and
 c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2NC(NR^{10})$—, CN, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_6$ alkyl, unsubstituted or substituted benzyl, unsubstituted or substituted aryl and unsubstituted or substituted heterocycle;

89

R[11] is independently selected from $C_1$–$C_6$ alkyl unsubstituted or substituted aryl and unsubstituted or substituted heterocycle;

R[12] is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;

W is imidazolyl;

V is phenyl;

X is selected from —C(O)—, —C(O)NR[10]—, —NR[10]C(O)—, —NR[10]C(O)—O—, —O—C(O)NR[10]—, —NR[10]C(O)NR[10]—, O, —N(R[10])—, —S(O)$_2$N(R[10])—, —N(R[10])S(O)$_2$— and S(O)$_m$;

$Z^1$ is unsubstituted or substituted phenyl or unsubstituted or substituted naphthyl, wherein the substituted phenyl or naphthyl is substituted with one or more of:
1) $C_{1-8}$ alkyl, $C_{2-8}$ alkenyl or $C_{2-8}$ alkynyl, unsubstituted or substituted with:
   a) $C_{1-4}$ alkoxy,
   b) NR[6]R[7],
   c) $C_{3-6}$ cycloalkyl,
   d) aryl or heterocycle,
   e) HO,
   f) —S(O)$_m$R[4],
   g) —C(O)NR[6]R[7], or
   h) $C_{1-4}$ perfluoroalkyl;
2) substituted or unsubstituted aryl or substituted or unsubstituted heterocycle,
3) halogen,
4) OR[6],
5) NR[6]R[7],
6) CN,
7) NO$_2$,
8) CF$_3$,
9) —S(O)$_m$R[4],
10) —OS(O)$_2$R[4],
11) —C(O)NR[6]R[7],
12) —C(O)OR[6], or
13) $C_3$–$C_6$ cycloalkyl;

heterocycle or heterocyclic represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring;

substituted aryl, heterocycle and benzyl include moieties containing from 1 to 3 substituents, in addition to the point of attachment to the rest of the compound, said substituents selected from F, Cl, Br, CF$_3$, NH$_2$, N($C_1$–$C_6$ alkyl)$_2$, NO$_2$, CN, ($C_1$–$C_6$ alkyl)O—, (aryl)O—, —OH, ($C_1$–$C_6$ alkyl)S(O)$_m$—, ($C_1$–$C_6$ alkyl)C(O)NH—, H$_2$N—C(NH)—, ($C_1$–$C_6$ alkyl)C(O)—, ($C_1$–$C_6$ alkyl)OC(O)—, N$_3$, ($C_1$–$C_6$ alkyl)OC(O)NH—, phenyl, pyridyl, imidazolyl, oxazolyl, isoxazolyl, thiazolyl, thienyl, furyl, isothiazolyl and $C_1$–$C_{20}$ alkyl;

m is 0, 1 or 2;

n is 0;

p is 0 or 1;

q is 1 or 2;

90 r is 0 to 5;

s is independently 0, 1, 2 or 3;

t is 1, 2, 3, 4, 5, 6 or 7; and v is 2 to 6;

or a pharmaceutically acceptable salt or stereoisomer thereof.

2. The compound according to claim 1 which is:

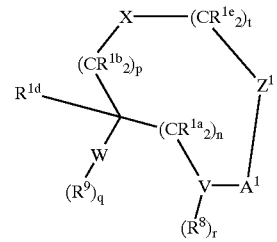

wherein:

$R^{1a}$, $R^{1b}$, $R^{1d}$ and $R^{1e}$ are independently selected from:
a) hydrogen,
b) aryl, heterocycle, $C_3$–$C_{10}$ cycloalkyl, R[10]O—, R[11]S(O)$_m$—, R[10]C(O)NR[10]—, (R[10])$_2$N—C(O)—, CN, NO$_2$, (R[10])$_2$NC(NR[10])—, (R[10])$_2$N—C(O)NR[10]—, R[10]C(O)—, R[10]OC(O)—, —N(R[10])$_2$, or R[11]OC(O)NR[10]—,
c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from unsubstituted or substituted aryl, heterocyclic, $C_3$–$C_{10}$ cycloalkyl, $C_2$–$C_6$ alkenyl, $C_2$–$C_6$ alkynyl, R[10]O—, R[11]S(O)$_m$—, R[10]C(O)NR[10]—, (R[10])$_2$N—C(O)—, CN, (R[10])$_2$N—C(NR[10])—, R[10]C(O)—, R[10]OC(O)—, —N(R[10])$_2$, and R[11]OC(O)—NR[10]—;

or two R[1e]s, on the same carbon atom may be combined to form —(CH$_2$)$_v$— wherein one of the CH$_2$ moieties is optionally replaced with —C(=O)—, —NH— or —NHC(=O)—;

$R^4$ is selected from $C_{1-4}$ alkyl, $C_{3-6}$ cycloalkyl, heterocycle, aryl, unsubstituted or substituted with:
a) $C_{1-4}$ alkoxy,
b) aryl or heterocycle,
c) halogen,
d) HO,
e)

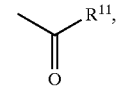

f) —SO$_2$R[11], or
g) N(R$_{10}$)$_2$;

$R^6$ and $R^7$ are independently selected from H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle, c) halogen,
d) HO,
e)

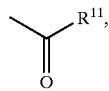

f) —SO$_2$R$^{11}$, or
g) N(R$^{10}$)$_2$, or
R$^6$ and R$^7$ may be joined in a ring;
R$^8$ is independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, C$_1$–C$_6$ perfluoroalkyl, F, Cl, Br, R$^{12}$O—, R$^{11}$S(O)$_m$—, R$^{10}$C(O)NR$^{10}$—, (R$^{10}$)$_2$NC(O)—, R$^{10}$$_2$N—C(NR$_{10}$)—, CN, NO$_2$, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, —N(R$^{10}$)$_2$, or R$^{10}$OC(O)NH—;
R$^9$ is selected from:
  a) hydrogen,
  b) C$_2$–C$_6$ alkenyl, C$_2$–C$_6$ alkynyl, C$_1$–C$_6$ perfluoroalkyl, F, Cl, Br, R$^{10}$O—, R$^{11}$S(O)$_m$—, R$^{10}$C(O)NR$_{10}$—, (R$^{10}$)$_2$NC(O)—, R$^{10}$$_2$N—C(NR$^{10}$)—, CN, NO$_2$, R$^{10}$C(O)—, R$^{10}$OC(O)—, —N(R$^{10}$)$_2$, or R$^{11}$OC(O)NR$^{10}$—, and
  c) C$_1$–C$_6$ alkyl unsubstituted or substituted by C$_1$–C$_6$ perfluoroalkyl, F, Cl, Br, R$^{10}$O—, R$^{11}$S(O)$_m$—, CN, R$^{10}$C(O)NR$^{10}$—, (R$^{10}$)$_2$NC(O)—, R$^{10}$$_2$N—C(NR$^{10}$)—, R$^{10}$C(O)—, R$^{10}$OC(O)—, —N(R$^{10}$)$_2$ or R$^{11}$OC(O)NR$^{10}$—;
R$^{10}$ is independently selected from hydrogen, C$_1$–C$_6$ alkyl, benzyl, unsubstituted or substituted aryl and unsubstituted or substituted heterocycle;
R$^{11}$ is independently selected from C$_1$–C$_6$ alkyl unsubstituted or substituted aryl and unsubstituted or substituted heterocycle;
R$^{12}$ is independently selected from hydrogen, C$_1$–C$_6$ alkyl, C$_1$–C$_3$ perfluoroalkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;
A$^1$ is O;
W is imidazolyl;
V is phenyl;
X is selected from —C(O)—, —C(O)NR$^{10}$—, —NR$^{10}$C(O)—, —NR$^{10}$C(O)—O—, —O—C(O)NR$^{10}$—, —NR$^{10}$C(O)NR$^{10}$—, O, —N(R$^{10}$)—, —S(O)$_2$N(R$^{10}$)—, —N(R$^{10}$)S(O)$_2$— and S(O)$_m$;
Z$^1$ is unsubstituted or substituted phenyl or unsubstituted or substituted naphthyl, wherein the substituted phenyl or naphthyl is substituted with one or more of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;
heterocycle or heterocyclic represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring;
substituted aryl, heterocycle and benzyl include moieties containing from 1 to 3 substituents, in addition to the point of attachment to the rest of the compound, said substituents selected from F, Cl, Br, CF$_3$, NH$_2$, N(C$_1$–C$_6$ alkyl)$_2$, NO$_2$, CN, (C$_1$–C$_6$ alkyl)O—, (aryl)O—, —OH, (C$_1$–C$_6$ alkyl)S(O)$_m$—, (C$_1$–C$_6$ alkyl)C(O)NH—, H$_2$N—C(NH)—, (C$_1$–C$_6$ alkyl)C(O)—, (C$_1$–C$_6$ alkyl)OC(O)—, N$_3$, (C$_1$–C$_6$ alkyl)OC(O)NH—, phenyl, pyridyl, imidazolyl, oxazolyl, isoxazolyl, thiazolyl, thienyl, furyl, isothiazolyl and C$_1$–C$_{20}$ alkyl;
m is 0, 1 or 2;
n is 0;
p is 0 or 1;
q is 1 or 2;
r is 0 to 5;
s is independently 0, 1, 2 and 3;
t is 1, 2, 3, 4, 5, 6 or 7; and
v is 2 to 6;
or a pharmaceutically acceptable salt or stereoisomer thereof.

3. The compound according to claim 1 which is:

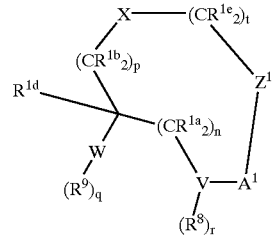

A1 wherein:
R$^{1a}$ and R$^{1b}$ are independently selected from hydrogen and C$_1$–C$_6$ alkyl;
R$^{1d}$ and R$^{1e}$ are independently selected from:
  a) hydrogen,
  b) aryl, heterocycle, C$_3$–C$_{10}$ cycloalkyl, R$^{10}$O— or —N(R$^{10}$)$_2$, and
  c) unsubstituted or substituted C$_1$–C$_6$ alkyl, unsubstituted or substituted C$_2$–C$_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from: unsubstituted or substituted aryl, heterocycle, $C_3$–$C_{10}$ cycloalkyl, $C_2$–$C_6$ alkenyl, $R^{10}O$— and —$N(R^{10})_2$;

or two $R^{1e}$s, on the same carbon atom may be combined to form —$(CH_2)_v$—, wherein one of the $CH_2$ moieties is optionally replaced with —$C(=O)$—, —NH— or —NHC$(=O)$—;

$R^4$ is selected from $C_{1-4}$ alkyl and $C_{3-6}$ cycloalkyl, unsubstituted or substituted with:
  a) $C_{1-4}$ alkoxy,
  b) halogen, or
  c) aryl or heterocycle;

$R^6$ and $R^7$ are independently selected from H; $C_{1-4}$ alkyl, $C_{3-6}$ cycloalkyl, aryl and heterocycle, unsubstituted or substituted with:
  a) $C_{1-4}$ alkoxy,
  b) halogen, or
  c) aryl or heterocycle;

$R^8$ is independently selected from:
  a) hydrogen,
  b) unsubstituted or substituted aryl, unsubstituted or substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by: unsubstituted or substituted aryl, unsubstituted or substituted heterocycle, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$, CN, $NO_2$, $(R^{10})_2NC(NR^{10})$—, $R^{10}C(O)$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl, unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;
V is phenyl;
W is imidazolyl;
X is selected from —$C(O)$—, —$C(O)NR^{10}$—, —$NR^{10}C(O)$—, —$NR^{10}C(O)NR^{10}$—, O, —$N(R_{10})$—, —$S(O)_2N(R^{10})$, —$N(R^{10})S(O)_2$, and $S(O)_m$;
$Z^1$ is unsubstituted or substituted phenyl or unsubstituted or substituted naphthyl, wherein the substituted phenyl or naphthyl is independently substituted with one or two of:

1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$, or
    g) —$C(O)NR^6R^7$,
  2) aryl or heterocycle,
  3) halogen,
  4) $OR_6$,
  5) $NR^6R^7$,
  6) CN,
  7) $NO_2$,
  8) $CF^3$,
  9) —$S(O)_mR^4$,
  10) —$C(O)NR^6R^7$, or
  11) $C_3$–$C_6$ cycloalkyl;

heterocycle or heterocyclic represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring;

substituted aryl, heterocycle and benzyl include moieties containing from 1 to 3 substituents, in addition to the point of attachment to the rest of the compound, said substituents selected from F, Cl, Br, $CF_3$, $NH_2$, $N(C_1$–$C_6$ alkyl$)_2$, $NO_2$, CN, $(C_1$–$C_6$ alkyl$)O$—, (aryl)O—, —OH, $(C_1$–$C_6$ alkyl$)S(O)_m$—, $(C_1$–$C_6$ alkyl$)C(O)NH$—, $H_2N$—$C(NH)$—, $(C_1$–$C_6$ alkyl$)C(O)$—, $(C_1$–$C_6$ alkyl$)OC(O)$—, $N_3$, $(C_1$–$C_6$ alkyl$)OC(O)NH$—, phenyl, pyridyl, imidazolyl, oxazolyl, isoxazolyl, thiazolyl, thienyl, furyl, isothiazolyl and $C_1$–$C_{20}$ alkyl;

m is 0, 1 or 2;
n is 0;
p is 0 or 1;
q is 1 or 2;
r is 0 to 5;
s is independently 0, 1, 2 or 3;
t is 1, 2, 3, 4, 5, 6 or 7; and
v is 2 to 6;

or a pharmaceutically acceptable salt or stereoisomer thereof.

4. The compound according to claim 1 of the formula B1:

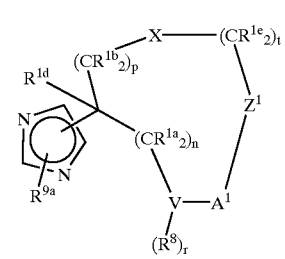

B1 wherein:
  $R^{1a}$ and $R^{1b}$ are independently selected from:
    a) hydrogen,
    b) aryl, heterocycle, cycloalkyl, $R^{10}O$—, —$N(R^{10})_2$ or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^{1d}$ and $R^{1e}$ are independently selected from:
a) hydrogen,
b) unsubstituted or substituted aryl, unsubstituted or substituted heterocycle, $C_3$–$C_{10}$ cycloalkyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$, $(R^{10})_2N$—C(O)$NR^{10}$—, $R^{10}C(O)$—, $R^{10}OC(O)$—, —$N(R^{10})_2$, or $R_{11}OC(O)NR^{10}$—,
c) unsubstituted or substituted $C_1$–$C_6$ alkyl, unsubstituted or substituted $C_2$–$C_6$ alkenyl or unsubstituted or substituted $C_2$–$C_6$ alkynyl, wherein the substituent on the substituted $C_1$–$C_6$ alkyl, substituted $C_2$–$C_6$ alkenyl or substituted $C_2$–$C_6$ alkynyl is selected from: unsubstituted or substituted aryl, heterocyclic, $C_3$–$C_{10}$ cycloalkyl, $C_2$–$C_6$ alkenyl, $C_2$–$C_6$ alkynyl, $CL$–$C_6$ perfluoroalkyl, halogen, $R^{10}O$—, $R^4S(O)_m$—, $R^4S(O)_2NR^{10}$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, —$N(R^{10})_2$, and $R^{11}OC(O)$—$NR^{10}$—;
or two $R^{1e}$s, on the same carbon atom may be combined to form —$(CH_2)_v$—, wherein one of the $CH_2$ moieties is optionally replaced with —C(=O)—, —NH— or —NHC(=O)—;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO,
e)

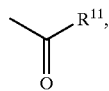

f) —$SO_2R^{11}$,
g) $N(R_{10})_2$, or
h) $C_{3-6}$ cycloalkyl;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R_{10})_2$, or $R^{11}OC(O)NR^{10}$—, and
c) $C_1$–$C_6$ alkyl substituted by: unsubstituted or substituted aryl, $C_1$–$C_6$ perfluoroalkyl, $R_{10}O$—, $R^{10}C(O)NR^{10}$—, $(R^{10})_2N$—$C(NR^{10})$—, $R^{10}C(O)$—, or $R^{11}OC(O)NR^{10}$—;

$R^{9a}$ is selected from hydrogen, $C_1$–$C_6$ alkyl and $C_1$–$C_6$ perfluoroalkyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;

V is phenyl;

X is selected from —C(O)—, —$C(O)NR^{10}$—, —$NR^{10}C(O)$—, —$NR^{10}C(O)NR^{10}$—, O, —$N(R^{10})$—, —$S(O)_2N(R^{10})$—, —$N(R^{10})S(O)_2$—, and $S(O)_m$;

$Z^1$ is unsubstituted or substituted phenyl or unsubstituted or substituted naphthyl, wherein the substituted phenyl or naphthyl is independently substituted with one or two of:
1) $C_{1-8}$ alkyl, $C_{2-8}$ alkenyl or $C_{2-8}$ alkynyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$,
g) —$C(O)NR^6R^7$, or
h) $C_{1-4}$ perfluoroalkyl;
2) substituted or unsubstituted aryl or substituted or unsubstituted heterocycle,
3) halogen,
4) $OR_6$,
5) $NR^6R^7$,
6) CN,
7) $NO_2$,
8) $CF^3$,
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

heterocycle or heterocyclic represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring;

substituted aryl, heterocycle and benzyl include moieties containing from 1 to 3 substituents, in addition to the point of attachment to the rest of the compound, said substituents selected from F, Cl, Br, $CF_3$, $NH_2$, $N(C_1$–$C_6$ alkyl$)_2$, $NO_2$, CN, $(C_1$–$C_6$ alkyl)O—, (aryl)O—, —OH, $(C_1$–$C_6$ alkyl$)S(O)_m$—, $(C_1$–$C_6$ alkyl)C(O)NH—, $H_2N$—C(NH)—, $(C_1$–$C_6$ alkyl)C(O)—, $(C_1$–$C_6$ alkyl)OC(O)—, $N_3$, $(C_1$–$C_6$ alkyl)OC(O)NH-, phenyl, pyridyl, imidazolyl, oxazolyl, isoxazolyl, thiazolyl, thienyl, furyl, isothiazolyl and $C_1$–$C_{20}$ alkyl;

m is 0, 1 or 2;

n is 0;

p is 0 or 1;

r is 0 to 5;

s is independently 0, 1, 2 or 3;

t is 1, 2, 3, 4, 5, 6 or 7; and v is 2 to 6;

or a pharmaceutically acceptable salt or stereoisomer thereof.

5. The compound according to claim 1 of the formula B1:

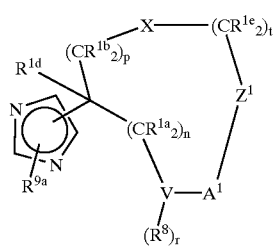

wherein:
R$^{1a}$ and R$^{1b}$ are independently selected from hydrogen or C$_1$–C$_6$ alkyl;
R$^{1d}$ and R$^{1e}$ are independently selected from:
  a) hydrogen,
  b) aryl, heterocycle, C$_3$–C$_{10}$ cycloalkyl, R$^{10}$O— or —N(R$^{10}$)$_2$, and
  c) C$_1$–C$_6$ alkyl, C$_2$–C$_6$ alkenyl or C$_2$–C$_6$ alkynyl, unsubstituted or substituted by aryl, heterocycle, C$_3$–C$_{10}$ cycloalkyl, C$_2$–C$_6$ alkenyl, R$^{10}$O—, or or two R$^{1e}$s on the same carbon atom may be combined to form —(CH$_2$)$_v$—, wherein one of the CH$_2$ moieties is optionally replaced with —C(=O)—, —NH— or —NHC(=O)—;
R$^4$ is selected from C$_{1-4}$ alkyl and C$_{3-6}$ cycloalkyl, unsubstituted or substituted with:
  a) C$_{1-4}$ alkoxy,
  b) halogen, or
  c) aryl or heterocycle;
R$^6$ and R$^7$ are independently selected from:
  a) hydrogen,
  b) C$_1$–C$_6$ alkyl, C$_2$–C$_6$ alkenyl, C$_2$–C$_6$ alkynyl, R$^{10}$C(O)— or R$^{10}$OC(O)— and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;
R$^8$ is independently selected from:
  a) hydrogen,
  b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$_{12}$O—, R$^{10}$C(O)NR$^{10}$—, CN, NO$_2$, (R$^{10}$)$_2$N—C(NR$^{10}$)—, R$^{10}$C(O)—, —N(R$_{10}$)$_2$, or R$^{11}$OC(O)NR$^{10}$—, and
  d) C$_1$–C$_6$ alkyl substituted by: unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;
R$^{9a}$ is selected from hydrogen, C$_1$–C$_6$ alkyl and C$_1$–C$_6$ perfluoroalkyl;
R$^{10}$ is independently selected from hydrogen, C$_1$–C$_6$ alkyl, benzyl and unsubstituted or substituted aryl;
R$^{11}$ is independently selected from Ci -C$_6$ alkyl and unsubstituted or substituted aryl;
R$^{12}$ is independently selected from hydrogen, C$_1$–C$_6$ alkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

A$^1$ is O;
V is phenyl;
X is selected from —C(O)—, —C(O)NR$^{10}$—, —NR$^{10}$C(O)—, —NR$^{10}$C(O)NR$^{10}$—, O, —N(R$^{10}$), S(O)$_2$N(R$^{10}$), —N(R$^{10}$)S(O)$_2$, and S(O)$_m$;
Z$^1$ is unsubstituted or substituted phenyl or unsubstituted or substituted naphthyl, wherein the substituted phenyl or naphthyl is independently substituted with one or two of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$_6$,
  5) NR$^6$R$^7$,
  6) CN,
  7) NO$_2$,
  8) CF$^3$,
  9) —S(O)$_m$R$^4$,
  10) —C(O)NR$^6$R$^7$, or
  11) C$_3$–C$_6$ cycloalkyl;
heterocycle or heterocyclic represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring;
substituted aryl, heterocycle and benzyl include moieties containing from 1 to 3 substituents, in addition to the point of attachment to the rest of the compound, said substituents selected from F, Cl, Br, CF$_3$, NH$_2$, N(C$_1$–C$_6$ alkyl)$_2$, NO$_2$, CN, (C$_1$–C$_6$ alkyl)O—, (aryl)O—, —OH, (C$_1$–C$_6$ alkyl)S(O)$_m$—, (C$_1$–C$_6$ alkyl)C(O)NH-, H$_2$N-C(NH)—, (C$_1$–C$_6$ alkyl)C(O)—, (C$_1$–C$_6$ alkyl)OC(O)—, N$_3$, (C$_1$–C$_6$ alkyl)OC(O)NH—, phenyl, pyridyl, imidazolyl, oxazolyl, isoxazolyl, thiazolyl, thienyl, furyl, isothiazolyl and C$_1$–C$_{20}$ alkyl;
m is 0, 1 or 2;
n is 0;
p is 0 or 1;
r is 0 to 5;
s is independently 0, 1, 2 or 3;
t is 1, 2, 3, 4, 5, 6 or 7; and
v is 2 to 6;
or a pharmaceutically acceptable salt or stereoisomer thereof.

6. A compound which is selected from:
5-(4-Cyano-8-methyl-10-oxo-2-oxa-9-aza-tricyclo[11.3.1.1$^{3,7}$]octadeca-1(16),3(18),4,6,13(17),14-hexaen-8-yl)-1-methyl-1H-imidazol-1-ium 2,2,2-trifluoroacetate;
5-(4-Cyano-8-methyl-10-oxo-2-oxa-9-aza-tricyclo[13.3.1.1$^{3,7}$]eicosa-1(18),3 (20),4,6,15(19),16-hexaen-8-yl)-1-methyl-1H-imidazol-1-ium 2,2,2-trifluoroacetate;
5-(4-Cyano-8-methyl-10-oxo-2-oxa-9-aza-tricyclo[15.3.1.1$^{3,7}$]docosa-1(20),3(22),4,6,17(21),18-hexaen-8-yl)-l1-methyl-1H-imidazol-1-ium 2,2,2-trifluoroacetate;
5-(4-Cyano-8-methyl-10-oxo-2-oxa-9-aza-(16-spiro-(2-cyclohexanone) tricyclo[15.3.1.1$^{3,7}$]docosa-1(20),3(22), 4,6,17(21),18-hexaen-8-yl)-1-methyl-1H-imidazol-1-ium 2,2,2-trifluoroacetate;

14-Amino-14-(3-methyl-3H-imidazol-4-yl)-2,9-dioxatricyclo[13.3.1.1$^{3,7}$]eicosa-1(18),3,5,7(20),15(19),16-hexaene-18-carbonitrile;

15-Amino-15-(3-methyl-3H-imidazol-4-yl)-2,9-dioxatricyclo[14.3.1.1$^{3,7}$]heneicosa-1(20),3,5,7(21),16.18-hexaene-19-carbonitrile;

14-amino-14-(3-methyl-3H-imidazol-4-yl)-2-oxa-10-azatricyclo[13.3.1.1$^{3,7}$]eicosa-1(18),3,5,7(20),15(19),16-hexaene-18-carbonitrile or a free base, a pharmaceutically acceptable salt or stereoisomers thereof.

7. The compound according to claim 6 which is 14-Amino-14-(3-methyl-3H-imidazol-4-yl)-2,9-dioxatricyclo[13.3.1.1$^{3,7}$]eicosa-1(18),3,5,7(20),15(19),16-hexaene-18-carbonitrile;

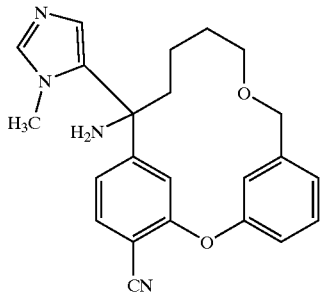

or a pharmaceutically acceptable salt or stereoisomer thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 6.

10. A method for inhibiting prenyl-protein transferase in a mammal with a mutation in the ras gene or a mutation in proteins which regulate ras activity, which comprises administering to said mammal a therapeutically effective amount of a composition of claim 8.

11. A method for inhibiting prenyl-protein transferase in a mammal with a mutation in the ras gene or a mutation in proteins which regulate ras activity, which comprises administering to said mammal a therapeutically effective amount of a composition of claim 9.

12. A method for treating cancer, said cancer consisting of colorectal carcinoma, exocrine pancreatic carcinoma and myeloid leukemias which comprises administering to a mammal in need thereof a therapeutically effective amount of a composition of claim 8.

13. A method for treating cancer, said cancer consisting of colorectal carcinoma, exocrine pancreatic carcinoma and myeloid leukemias which comprises administering to a mammal in need thereof a therapeutically effective amount of a composition of claim 9.

14. A method for treating neurofibromatosis which comprises administering to a mammal in need thereof a therapeutically effective amount of a composition of claim 8.

15. A method for treating blindness related to retinal vascularization which comprises administering to a mammal in need thereof a therapeutically effective amount of a composition of claim 8.

16. A method for treating infections from hepatitis delta which comprises administering to a mammal in need thereof a therapeutically effective amount of a composition of claim 8.

17. A method for preventing restenosis which comprises administering to a mammal in need thereof a therapeutically effective amount of a composition of claim 8.

18. A method for treating polycystic kidney disease which comprises administering to a mammal in need thereof a therapeutically effective amount of a composition of claim 8.

19. A method of conferring radiation sensitivity on a tumor cell using a therapeutically effective amount of a composition of claim 8 in combination with radiation therapy.

20. A method of using a therapeutically effective amount of a composition of claim 7 in combination with an antineoplastic to treat cancer.

21. A method according to claim 20 wherein the antineoplastic is paclitaxel.

22. A process for making a pharmaceutical composition comprising combining a compound of claim 1 and a pharmaceutically acceptable carrier.

\* \* \* \* \*